United States Patent
Soares Da Silva

(10) Patent No.: US 9,750,747 B2
(45) Date of Patent: Sep. 5, 2017

(54) TREATMENTS INVOLVING ESLICARBAZEPINE ACETATE OR ESLICARBAZEPINE

(75) Inventor: Patricio Manuel Vieira Araujo Soares Da Silva, São Mamede do Coronado (PT)

(73) Assignee: BAIL-PORTELA & CA, S.A., São Mamede do Coronado (PT)

(*) Notice: Subject to any disclaimer, the term of this patent is extended or adjusted under 35 U.S.C. 154(b) by 0 days.

(21) Appl. No.: 14/240,847

(22) PCT Filed: Aug. 24, 2012

(86) PCT No.: PCT/PT2012/000031
§ 371 (c)(1),
(2), (4) Date: Jul. 10, 2014

(87) PCT Pub. No.: WO2013/032351
PCT Pub. Date: Mar. 7, 2013

(65) Prior Publication Data
US 2014/0315821 A1    Oct. 23, 2014

Related U.S. Application Data

(60) Provisional application No. 61/527,887, filed on Aug. 26, 2011.

(51) Int. Cl.
| | |
|---|---|
| *A61K 31/55* | (2006.01) |
| *A61K 31/195* | (2006.01) |
| *A61K 31/4166* | (2006.01) |
| *A61K 31/4535* | (2006.01) |
| *A61K 31/515* | (2006.01) |
| *A61K 45/06* | (2006.01) |

(52) U.S. Cl.
CPC ............ *A61K 31/55* (2013.01); *A61K 31/195* (2013.01); *A61K 31/4166* (2013.01); *A61K 31/4535* (2013.01); *A61K 31/515* (2013.01); *A61K 45/06* (2013.01)

(58) Field of Classification Search
None
See application file for complete search history.

(56) References Cited

U.S. PATENT DOCUMENTS

2010/0297181 A1   11/2010   Hanada et al.

FOREIGN PATENT DOCUMENTS

| EP | 1767638 A2 | 3/2007 |
|---|---|---|
| WO | 97/02250 | 1/1997 |
| WO | 2004/071152 | 8/2004 |
| WO | 2006/120501 | 11/2006 |
| WO | 2006/121363 | 11/2006 |
| WO | 2007/094694 | 8/2007 |
| WO | 2008/088233 | 7/2008 |
| WO | 2009/054743 | 4/2009 |
| WO | 2009/082039 A1 | 7/2009 |
| WO | 2011/014084 | 2/2011 |
| WO | 2011/031176 | 3/2011 |
| WO | 2012/091593 | 7/2012 |

OTHER PUBLICATIONS

Almeida et al., Pharmacokinetics, Efficacy, and Tolerability of Eslicarbazepine Acetate in Children and Adolescents With Epilepsy, 2008, J Clin Pharmacol 48(8):966-977.*
International Search Report dated Oct. 29, 2012 from International Application No. PCT/PT2012/000031, pp. 1-4.
Karceski, Steven et al. Treatment of epilepsy in adults: expert opinion, 2005. Science Direct, Epilepsy & Behavior 7, 2005, pp. S1-S64.
Sierra-Paredes, German et al. Anticonvulsant effect of eslicarbazepine acetate (BIA 2-093) on seizures induced by microperfusion of picrotoxin in the hippocampus of freely moving rats. Epilepsy & Behavior 72, 2006, pp. 140-163.
McCabe, Paul H. New anti-epileptic drugs for the 21st century. Expert Opinion on Pharmacotherapy, 2000, pp. 1465-6566.
Sierra-Paredes, German et al. Effect of eslixarbazephine acetate (BIA 2-093) on latrunculin A-induced seizures and extracellular amino acid concentrations in the rat hippocampus. Epilepsy Research, 2007, 77, pp. 36-43.
Garnett, William R. Antiepileptic Drug Treatment: Outcomes and Adherence. Supplement to Pharmacotherapy, 2000, vol. 20, No. 8, pp. 191S-199S.
Almeida, Luis et al. Eslicarbazepine Acetate. The Treatment of Epilepsy, Chapter 38, 3rd Edition, EDS, 2009, pp. 485-498.
Liu, Lige et al. The Mechanism of Carbamazepine Aggravation of Absence Seizures. JPET, Aug. 8, 2006, 319: 1-38.
Zheng, Thomas et al. Oxcarbazepine, not its active metabolite, potentiates GABAA activation and aggravates absence seizures. Epilepsia, 2009, 50(1): 83-87.
Bialer, Meir et al. Key factors in the discovery and development of new antiepileptic drugs. Nature Review, Jan. 2010, vol. 9, pp. 68-82.
Ambrosio, Antonio F. et al. Inhibition of glutamate release by BIA 2-093 and BIA 2-024, two novel derivatives of carbamazepine, due to blockade of sodium but not calcium channels. Biochemical Pharmacology, 2001 (61): 1271-1275.
McCormack, Paul L. et al. Eslicarbazepine Acetate, Adis Drug Profile, CNS Drugs, 2009, 23(1): 71-79.
Cretin, Benjamin et al. Adjunctive antiepileptic drugs in adult epilepsy: how the first add-on could be last. Expert Opinion Pharmacotherapy, 2010, 11(7): 1053-1067.
Mestre, Tiago et al. Eslicarbazepinee acetate: a new option for the treatment of focal epilepsy. Expert Opinion Invest. Drugs, 2009, 18(2): 221-229.
Gelisse, Philippe et al. Worsening of Seizures by Oxcarbazepine in Juvenile Idiopathic Generalized Epilepsies. Epilepsia, 2004, 45(1): 1282-1286.

(Continued)

*Primary Examiner* — John Ulm
(74) *Attorney, Agent, or Firm* — MH2 Technology Law Group, LLP

(57) ABSTRACT

The invention provides a drug selected from eslicarbazepine acetate and eslicarbazepine, for use in treating or preventing a disorder selected from epilepsy, affective disorders, schizoaffective disorders, bipolar disorders, neuropathic pain and neuropathic pain related disorders, attention disorders, anxiety disorders, sensorimotor disorders, vestibular disorders, and fibromyalgia, in a patient suffering from or susceptible to absence seizures.

19 Claims, 3 Drawing Sheets

(56) References Cited

OTHER PUBLICATIONS

CHMP Assessment Report for Zebinix (International Nonproprietary Name: eslicarbazepine acetate Procedure No. EMEA/H/C/000988, Feb. 19, 2009, pp. 1-80.

Benes, Jan et al. Anticonvulsant and Sodium Channel-Blocking Properties of Novel 10,11-Dihydro-5H-dibenz[b,f] azepine-5-carboxamide Derivatives. J. Med. Chem., 1999 (42): 2582-2587.

Perucca, Emilio et al. Development of new antiepileptic drugs: challenges, incentives and recent advances. Lancet Neurology, Sep. 2007, vol. 6, pp. 793-804.

Milovan, Denise et al. Effect of eslicarbazepine acetate and oxcarbazepine on cognition and psychomotor function in healthy volunteers. Epilepsy & Behavior, Aug. 2010, vol. 18, Issue 14, pp. 366-373.

Rauchenzauner, Markus et al. Update on treatment of partial onset epilepsy: role of eslicarbazepine. Neuropsychiatric Disease and Treatment, 2010(6): 723-730.

Vohora, D. et al. Recent Advances in Adjunctive Therapy for Epilepsy: Focus on Sodium Channel Blockers as Third-Generation Antiepileptic Drugs. Drugs of Today, 2010, 46(4): 265-277.

Ben-Menachem, E. et al. Eslicarbazepine acetate as adjunctive therapy in adult patients with partial epilepsy. Epilepsy Research, 2010(89): 278-285.

Halasz, Peter et al. Long-term efficacy and safety of eslicarbazepine acetate: Results of a I-year open-label extension study in partial-onset seizures in adults with epilepsy. Epilepsia, 2010, 51(10): 1963-1969.

Maia et al, BIA 2-093 as add-on therapy in refractory partial epilepsy in adults, Epilepsia (2004) vol. 45(3), p. 158.

Bialer et al, Progress report on new antiepileptic drugs: a summary of the Seventh Eilat Conference (EILAT VII), Epilepsy Research 61 (2004), pp. 1-48.

Almeida et al, Double-blind, add-on, placebo-controlled exploratorytrialofeslicarbazepineacetateinpatients with partial-onset seizures, Epilepsia, 46 (Suppl. 8):1-373, (2005), pp. 1 and 167-168.

Bialer, New antiepileptic drugs that are second generation to existing antiepileptic drugs, Expert Opin. Investig. Drugs (2006) 15(6), pp. 637-647.

Nunes et al, Pharmacokinetics of eslicarbazepine acetate in children and adolescents with epilepsy, Epilepsia, 48 (Suppl. 7):2-177, (2007), pp. 1 and 143.

Almeida et al, Eslicarbazepine Acetate (BIA 2-093), Neurotherapeutics, vol. 4, pp. 88-96, (2007).

Elger et al, Eslicarbazepine Acetate: A Double-blind, Add-on, Placebo-controlled Exploratory Trial in Adult Patients with Partial-onset Seizures, Epilepsia, 48(3):497-504, (2007), pp. 497-504.

Ben-Menachem et al, Efficacy and safety of eslicarbazepine acetate (ESL) as add-on treatment in adults with refractory partial-onset seizures: BIA-2093-302 study, Epilepsia, 49 (suppl. 7):424, (2008), pp. 1, and 424-425.

Shorvon et al., "The Treatment of Epilepsy", 3rd edition,eds. Shorvon, Perucca & Engel, Chapter 38, 2009, pp. 1-16.

Bialer et al, Investigation of the influence of eslicarbazepine acetate on the plasma concentrations of concomitant antiepileptic drugs in patients with partial epilepsy, Epilepsia, 50 (Suppl. 4): 2-262, (2009), pp. 1 and 156.

Cramer et al, Improvement in quality-of-life and depressive symptoms during long-term treatment with eslicarbazepine acetate: BIA-2093-301 study, Epilepsia, 49 (suppl. 7):1-498, 2008, pp. 1 and 426-427.

Cramer et al, Quality-of-life improvement during longterm treatment with eslicarbazepine acetate, Epilepsia, 50 (Suppl. 4): 2-262, 2009, pp. 1 and 124.

Czapinski et al, Efficacy and safety of eslicarbazepine acetate (ESL) as add-on treatment in adults with refractory partial-onset seizures: BIA-2093-301 study, Epilepsia, 49 (suppl. 7):1-498, 2008, pp. 1 and 428.

Elger et al, Efficacy and safety of eslicarbazepine acetate as add-on treatment in patients with partial-onset seizures: pooled analysis of three double-blind phase III clinical studies, Epilepsia, 49 (suppl. 7):1-498, 2008, pp. 1 and 128-429.

Elger et al, Efficacy and safety of eslicarbazepine acetate as add-on treatment in adults with refractory partial-onset seizures: BIA-2093-301 study, Epilepsia, 50 (Suppl. 4): 2-262, 2009, pp. 1 and 71.

Fuseau et al, Population pharmacokinetics of eslicarbazepine acetate in adult patients with refractory partial seizures, Epilepsia, 49 (suppl. 7):1-498, 2008, pp. 1 and 432.

Gabbai et al, Long-term treatment of partial epilepsy with eslicarbazepine acetate (ESL): results of a one-year open-label extension of study BIA-2093-302, Epilepsia, 49 (suppl. 7):1-498, 2008, pp. 1 and 432-433.

Gil-Nagel et, Efficacy and safety of eslicarbazepine acetate (ESL) as add-on treatment in adults with refractory partial-onset seizures: BIA-2093-303 study, Epilepsia, 49 (suppl. 7):1-498, 2008, pp. 1 and 433-434.

Guekht et al, Long-term treatment of partial epilepsy with eslicarbazepine acetate: results of a 1-year open-label extension study, Epilepsia, 50 (Suppl. 4): 2-262, 2009, pp. 1 and 106.

Halaz et al, Long-term treatment of partial epilepsy with eslicarbazepine acetate (ESL): results of a one-year open-label extension to study BIA-2093-301, Epilepsia, 49 (suppl. 7):1-498, 2008, pp. 1 and 435-436.

Hodoba et al, Depressive symptoms improvement during long-term treatment with eslicarbazepine acetate, Epilepsia, 50 (Suppl. 4): 2-262, 2009, pp. 1 and 126.

Hufnagel et al, Efficacy and safety of eslicarbazepine acetate as add-on treatment in adults with refractory partial-onset seizures: BIA-2093-302 study, Epilepsia, 50 (Suppl. 4): 2-262, 2009, pp. 1 and 104.

Lopes Lima et al, Long-term treatment of partial epilepsywith eslicarbazepine acetate (ESL): results of a one-year open-label extension of study BIA-2093-303, Epilepsia, 49 (suppl. 7):1-498, 2008, pp. 1 and 441-442.

Lopes Lima et al, Efficacy and safety of eslicarbazepine acetate as add-on treatment in adults with refractory partial-onset seizures: BIA-2093-303 study, Epilepsia, 50 (Suppl. 4): 2-262, 2009, pp. 1 and 106.

Maia et al, Dose-response population analysis of eslicarbazepine acetate in adult patients with refractory partial apilepsy, Epilepsia, 49 (suppl. 7):1-498, 2008, pp. 1 and 443.

Pereira et al, Improvement in quality-of-life and depressive symptoms during long-term treatment with eslicarbazepine acetate: BIA-2093-303 study, Epilepsia, 49 (suppl. 7):1-498, 2008, pp. 1 and 446-448.

"Summary of Product Characteristics (SMPC) for the product carbamazepine-containing Tegretol", Novartis Pharmaceuticals Corporation, T2011-31/T2011-32, Mar. 2011, 22 pages.

Perucca et al, Pharmacokinetics of eslicarbazepine acetate at steady-state in adults with epilepsy, Epilepsia, 50 (Suppl. 4): 2-262, 2009, pp. 1 and 196.

"Pharmacokinetics, Efficacy and Tolerability of BIA 2-093", Clinical trial NCT02170064, received Jun. 20, 2014 and last updated Aug. 29, 2014 and printed from https://clinicaltrials.gov/ct2/show/study/NCT02170064, 11 pages.

Soares Da Silva et al, Improvement in quality-of-life and depressive symptoms during long-term treatment with eslicarbazepine acetate: BIA-2093-302 study, Epilepsia, 49(suppl. 7):1-498, 2008, pp. 1 and 455-456.

Almeida et al, Pharmacokinetics, Efficacy, and Tolerability of Eslicarbazepine Acetate in Children and Adolescents with Epilepsy, J. Clin. Pharmacol. 2008; 48; 966, pp. 966-977.

Elger et al, Efficacy and safety of eslicarbazepine acetate as adjunctive treatment in adults with refractory partial-onset seizures: A randomized, double-blind, placebo-controlled, parallel-group phase III study, Epilepsia, 50 (3):454-463, 2009, pp. 454-463.

Gil-Nagel et al, Efficacy and safety of 800 and 1200 mg eslicarbazepine acetate as adjunctive treatment in adults with refractory partial-onset seizures, Acta Neurol Scand 2009: 120: pp. 281-287.

(56) References Cited

OTHER PUBLICATIONS

Maia et al, BIA 2-093 as add-on therapy in refractory partial epilepsy in adults, European Congress on Epilepsy 2004, 1 page.
Ben-Menachem et al, Efficacy and safety of eslicarbazepine acetate (ESL) as add-on treatment in adults with refractory partial-onset seizures: BIA-2093-302 study, 2008 Annual Meeting of the American Epilepsy Society, 1 page.
Bialer et al, Investigation of the influence of eslicarbazepine acetate on the plasma concentrations of concomitant antiepileptic drugs in patients with partial epilepsy, 8th European Congress on Epileptology, 2008, 1 page.
Cramer et al, Quality-of-life improvement during long-term treatment with eslicarbazepine acetate, 8th European Congress on Epileptology, 2008, 1 page.
Cramer et al, Improvement in Quality-Of-Life and Depressive Symptoms During Long-Term Treatment with Eslicarbazepine Acetate: BIA-2093-301 Study, 2008 Annual Meeting of the American Epilepsy Society, 1 page.
Elger et al, Efficacy and safety of eslicarbazepine acetate as add-on treatment in adults with refractory partial-onset seizures: BIA-2093-301 Study, 8th European Congress on Epileptology, 2008, 1 page.
Elger et al, Efficacy and Safety of Eslicarbazepine Acetate as Add-On Treatment in Patients with Partial-Onset Seizures: Pooled Analysis of Three Double-Blind Phase III Clinical Studies, 2008 Annual Meeting of the American Epilepsy Society, 1 page.
Falcao et al, Population Pharmacokinetics of AEDs after Co-Administration with Eslicarbazepine Acetate in Adult atients with Refractory Partial Epilepsy, 2008 Annual Meeting of the American Epilepsy Society, 1 page.
Fuseau et al, Population Pharmacokinetics of Eslicarbazepine Acetate in Adult Patients with Refractory Partial Seizures, 2008 Annual Meeting of the American Epilepsy Society, 1 page.
Gabbai et al, Long-Term Treatment of Partial Epilepsy with Eslicarbazepine Acetate (ESL): Results of a One-Year Open-Label Extension of Study BIA-2093-302, 2008 Annual Meeting of the American Epilepsy Society, 1 page.
Gil-Nagel et al, Efficacy and Safety of Eslicarbazepine Acetate (ESL) as Add-On Treatment in Adults with Refractory Partial-Onset Seizures: BIA-2093-303 Study, 2008 Annual Meeting of the American Epilepsy Society, 1 page.
Guekht et al, Long-term treatment of partial epilepsy with eslicarbazepine acetate: results of a 1-year open-label extension study, 8th European Congress on Epileptology, 2008, 1 page.
Halasz et al, Long-Term Treatment of Partial Epilepsy with Eslicarbazepine Acetate (ESL): Results of a One-Year Open-Label Extension to Study BIA-2093-301, 2008 Annual Meeting of the American Epilepsy Society, 1 page.
Hodoba et al, Depressive symptoms improvement during long-term treatment with eslicarbazepine acetate, 8th European Congress on Epileptology, 2008, 1 page.
Hufnagel et al, Efficacy and safety of eslicarbazepine acetate as add-on treatment in adults with refractory partial-onset seizures: BIA-2093-302 Study, 8th European Congress on Epileptology, 2008, 1 page.
Lopes Lima et al, Efficacy and safety of eslicarbazepine acetate as add-on treatment in adults with refractory partial-onset seizures: BIA-2093-303 Study, 8th European Congress on Epileptology, 2008, 1 page.
Lopes Lima et al, Long-Term Treatment of Partial Epilepsy with Eslicarbazepine Acetate (ESL): Results of a One-Year Open-Label Extension of Study BIA-2093-303, 2008 Annual Meeting of the American Epilepsy Society, 1 page.
Maia et al, Dose-Response Population Analysis of Eslicarbazepine Acetate in Adult Patients with Refractory Partial Epilepsy, 2008 Annual Meeting of the American Epilepsy Society, 1 page.
Perucca et al, Pharmacokinetics of eslicarbazepine acetate at steady-state in adults with epilepsy, 8th European Congress on Epileptology, 2008, 1 page.
Almeida et al, A double-blind, add-on, placebo-controlled exploratory trial of eslicarbazepine acetate in patients with partial-onset seizures, 2008 Annual Meeting of the American Epilepsy Society, 1 page.
Versavel et al, Long-term treatment of partial epilepsy with eslicarbazepine acetate (ESL): Results of a one year pen label extension to study BIA-2093-301, Neurology 72 (Suppl.3): A351, 2009, 1 page.
Versavel et al, An evaluation of the efficacy and safety of eslicarbazepine acetate (ESL) as add-on treatment in adults with refractory partial onset seizures: BIA 2093 Study, Neurology 72 (Suppl.3): A352, 2009, 1 page.
Almeida et al., "Eslicarbazepine Acetate", The Treatment of Epilepsy, 3rd Edition, 2009, pp. 485-498.
Bialer et al., "Investigation of the Influence of Eslicarbazepine Acetate on the Plasma Concentrations of Concomitant Antiepileptic Drugs in Patients With Partial Epilepsy", Epilepsia, 2009, vol. 50, Suppl. 4, p. 156.
Cramer et al., "Quality-Of-Life Imporivement During Long-Term Treatment With Eslicarbazepine Acetate", Epilepsia, 2009, vol. 50, Suppl. 4, 2009, p. 124.
Elger et al., "Efficacy and Safety of Eslicarbazepine Acetate As Add-On Treatment in Adults With Refractory Partial-Onset Seizures: BIA-2093-301 Study", Epilepsia, 2009, vol. 50, Suppl. 4, p. 71.
Elger et al., "Efficacy and safety of eslicarbazepine acetate as adjunctive treatment in adults with refractory partial-onset seizures: A randomized, double-blind, placebo-controlled, parallel-group phase III study", Epilepsia, 2009, vol. 50, No. 3, pp. 454-463.
Gil Nagel et al., "Efficacy and safety of 800 and 1200 mg eslicarbazepine acetate as adjunctive treatment in adults with refractory partial-onset seizures", Acta Neural Scand, 2009, vol. 120, pp. 281-287.
Guekht et al., "Long-Term Treatment of Partial Epilepsy With Eslicarbazepine Acetate: Results of a 1-Year Open-Label Extension Study", Epilepsia, 2009, vol. 50, Suppl. 4, p. 106.
Hodoba et al, "Depressive Symptoms Improvement During Long-Term Treatment With Eslicarbazepine Acetate", Epilepsia, 2009, vol. 50, Suppl. 4, p. 126.
Hufnagel et al, "Efficacy and Safety of Eslicarbazepine Acetate As Add-On Treatment in Adults With Refractory Partial-Onset Seizures: BIA-2093-302 Study", Epilepsia, 2009, vol. 50, Suppl. 4, p. 104.
Lopes-Lima et al, "Efficacy and Safety of Eslicarbazepine Acetate As Add-On Treatment in Adults With Refractory Partial-Onset Seizures: BIA-2093-303 Study", Epilepsia, 2009, vol. 50, Suppl. 4, p. 106.
McCormack et al., "Eslicarbazepine Acetate", CNS Drugs, 2009, vol. 23, No. 1, pp. 71-79.
Mestre et al., "Eslicarbazepine acetate: a new option for the treatment of focal epilepsy", Expert Opin. Investig. Drugs, 2009, vol. 18, No. 2, pp. 221-229.
Perucca et al., "Pharmacokinetics of Eslicarbazepine Acetate At Steady-State in Adults With Epilepsy", Epilepsia, 2009, vol. 50, Suppl. 4, p. 196.
Tripp et al., "An Investigation of the Effect of Eslicarbazepine Acetate on Cardiac Repolarization: A Pooled Analysis of Over-Read Electrocardiograms From Three Double-Blind Phase III Clinical Studies", Epilepsia, 2009, vol. 50, Suppl. 11, pp. 109-111.
Versavel et al., "Long-Term Treatment of Partial Epilepsy with Eslicarbazepine Acetate (ESL): Results of a One-Year Open-Label Extension to Study BIA-2093-301", Neurology, Mar. 17, 2009, vol. 72, Suppl. 3, p. A351.
Versavel et al., "An Evaluation of the Efficacy and Safety of Eslicarbazepine Acteate (ESL) as Add-On Treatment in Adults with Refractory Partial-Onset Seizures: BIA-2093 Study", Neurology, Mar. 17, 2009, vol. 72, Suppl. 3, p. A352.
Bialer et al., "A double-blind, adjunct, placebo-controlled exploratory trial of once-daily vs. Twice-daily eslicarbazepine acetate in subjects with partial onset seizures", 64th Annual American Epilepsy Society Meeting, Dec. 3-7, 2010, 1 page.

(56) References Cited

OTHER PUBLICATIONS

Bialer et al., "Investigation of the influence of eslicarbazepine acetate on the plasma concentrations of concomitant antiepileptic drugs in subjects with partial onset seizures", 64th Annual American Epilepsy Society Meeting, Dec. 3-7, 2010, 1 page.
Trinka et al., "An evaluation of the efficacy and safety of eslicarbazepine acetate as adjunct treatment in adults with refractory partial onset seizures: Study BIA-2093-301", 64th Annual American Epilepsy Society Meeting, Dec. 3-7, 2010, 1 page.
Halasz et al., "Long-term treatment of partial onset seizures with eslicarbazepine acetate: Results of a one-year open-label extension of study BIA-2093-301", 64th Annual American Epilepsy Society Meeting, Dec. 3-7, 2010, 1 page.
Halasz et al., "Long-term treatment of partial onset Seizures with eslicarbazepine acetate as adjunctive therapy", 64th Annual American Epilepsy Society Meeting, Dec. 3-7, 2010, 1 page.
Ben-Menachem., "Evaluation of efficacy and safety of eslicarbazepine acetate as adjunct treatment in adults with refractory partial onset seizures: Study BIA-2093-302", 64th Annual American Epilepsy Society Meeting, Dec. 3-7, 2010, 1 page.
Carrero et al., "Long-term treatment of partial oset seizures with eslicarbazepine acetate: Results of a one-year open-label extension of study BIA-2093-302", 64th Annual American Epilepsy Society Meeting, Dec. 3-7, 2010, 1 page.
Cramer et al., "Assessment of quality-of-life during two, phase III, open-label, long-term extension studies with aslicarbazepine acetate: Studies BIA-2093-301 and BIA-2093-302", 64th Annual American Epilepsy Society Meeting, Dec. 3-7, 2010, 1 page.
Tripp et al., "An investigation of the effect of eslicarbazepine acetate on cardiac repolarization: A pooled analysis of over-read electrocardiograms from two double-blind phase III clinical studies", 64th Annual American Epilepsy Society Meeting, Dec. 3-7, 2010, 1 page.
Versavel et al., "An investigation of the effects of eslicarbazepine acetate on hyponatremia: A pooled analysis of two double-blind phase III clinical studies", 64th Annual American Epilepsy Society Meeting, Dec. 3-7, 2010, 1 page.
Zummo et al., "An evaluation of the effect of eslicarbazepine acetate on weight, glucose, and lipids: An integrated analysis of two double-blind phase III clinical studies", 64th Annual American Epilepsy Society Meeting, Dec. 3-7, 2010, 1 page.
Versavel et al., "An exploratory, subgroup analysis of the safety and efficacy of eslicarbazepine acetate administered once daily as concomitant treatment to levetiracetam: An integrated analysis of two phase III studies", 64th Annual American Epilepsy Society Meeting, Dec. 3-7, 2.010, 1 page.
"Double-blind, randomized, historical control study of safety and efficacy of eslicarbazepine acetate monotherapy in subjects with partial epilepsy not well controlled by current AEDs", 64th Annual American Epilepsy Society Meeting, Dec. 3-7, 2010, 1 page.
"Efficacy and safety of eslicarbazepine Acetate (BIA 2-093) as adjunctive therapy for refractory partial seizures in a Double-blind, randomised, placebo-controlled, parallel-group, multicentre clinical trial", 64th Annual American Epilepsy Society Meeting, Dec. 3-7, 2010, 1 page.
Perucca et al., "Assessment of the impact of eslicarbazepine acetate on carbamazepine pharmacokinetics at steady-state: A pooled analysis of three placebo-controlled phase III studies", 9th European Congress on Epileptology, Jun. 27-Jul. 1, 2010, 1 page.
Cramer et al., "Depressive symptoms improve with 1-year eslicarbazepine acetate treatment: a pooled analysis of three open-label extensions of phase III studies in patients with partial-onset seizures", 9th European Congress on Epileptology, Jun. 27-Jul. 1, 2010, 1 page.
Gil-Nagel et al., "An investigation of the effect of eslicarbazepine acetate on cardiac repolarization: A pooled analysis of over-read electrocardiograms from three double-blind phase III clinical studies", 9th European Congress on Epileptology, Jun. 27-Jul. 1, 2010, 1 page.
Maia et al., "Seizure freedom and patient retention with adjunctive eslicarbazepine acetate therapy in adults with -efractory partial seizures during three randomised, double-blind, placebo-controlled trials with 1-year, open-label extensions", 9th European Congress on Epileptology, Jun. 27-Jul. 1, 2010, 1 page.
Nunes et al., "Incidence of rash and hyponatraemia in adult patients with refractory partial seizures treated with adjunctive eslicarbazepine acetate: Results from three phase III studies and 1-year open-label extensions", 9th European Congress on Epileptology, Jun. 27-Jul. 1, 2010, 1 page.
Ben-Menachem et al., "Eslicarbazepine acetate as adjunctive therapy in adult patients with partial epilepsy", Epilepsy Research, 2010, vol. 89, pp. 1-9.
Elinor Ben-Menachem, "Eslicarbazepine acetate: A well-kept secret?", Epilepsy Currents, 2010, vol. 10, No. 1, pp. 7-8.
Brown et al., "Role of eslicarbazepine in the treatment of epilepsy in adult patients with partial-onset seizures", Therapeutics and Clinical Risk Management, Mar. 11 2010, vol. 6, pp. 103-109.
Halasz et al., "Long-term efficacy and safety of eslicarbazepine acetate: Results of a 1-year open-label extension study in partial-onset seizures in adults with epilepsy", Epilepsia, 2010, pp. 1-7.
Landmark et al., "Pharmacological management of epilepsy: Recent advances and future prospects", Drugs, 2008, vol. 68, No. 14, pp. 1925-1939.
Landmark et al., "Drug interactions involving the new second- and third-generation antiepileptic drugs", Expert Rev. Neurother, 2010, vol. 10, Issue 1, pp. 119-140.
Richard T. Owen, "Eslicarbazepine acetate: A novel agent for the adjunctive treatment of epilepsy", Drugs of Today, 2010, vol. 46, Issue 1, pp. 23-31.
Rauchenzauner et al., "Update on treatment of partial onset epilepsy: Role of eslicarbazepine", Neuropsychiatric Disease and Treatment, Nov. 1 2010, vol. 6, p. 723-730.
Schmitz et al., "Assessing the unmet treatment need in partial-onset epilepsy: Looking beyond seizure control", Epilepsia, vol. 51, Issue 11, 2010, pp. 2231-2240.
Vohora et al., "Recent advances in adjunctive therapy for epilepsy: focus on sodium channel blockers as third generation antiepileptic drugs", Drugs of Today, 2010, vol. 46, Issue 4, pp. 265-277.
Steinhoff et al., "Tolerability of eslicarbazepine acetate by treatment phase in adults with refractory partial seizures: A Combined analysis of three randomized, double-blind, placebocontrolled trials", 9th European Congress on Epileptology in Epilepsia, Jun. 27-Jul. 1, 2010, Rhodes, Greece, vol. 51, Suppl. 4, 2 pages.
Elger et al., "An evaluation of the effect of eslicarbazepine acetate on metabolic parameters: A pooled analysis of three Double-blind Phase III clinical studies", 9th European Congress on Epileptology in Epilepsia, Jun. 27-Jul. 1, 2010, Rhodes, Greece, vol. 51, Suppl. 4, 2 pages.
Nunes et al., "Incidence of rash and hyponatraemia in adult patients with refractory partial seizures treated with adjunctive eslicarbazepine acetate: Results from three Phase III studies and 1-year open-label extensions", 9th European Congress on Epileptology in Epilepsia, Jun. 27-Jul. 1, 2010, Rhodes, Greece, vol. 51, Suppl. 4, 3 pages.
Cramer et al., "Depressive symptoms improve with 1-year eslicarbazepine acetate treatment: A pooled analysis of 3 open-label extensions of Phase III studies in patients with partialonset seizures", 9th European Congress on Epileptology in Epilepsia, Jun. 27-Jul. 1, 2010, Rhodes, Greece, vol. 51, Suppl. 4, 2 pages.
Perucca et al., "Assessment of the impact of eslicarbazepine acetate on carbamazepine pharmacokinetics at steady-state: a pooled analysis of three placebo-controlled Phase III studies", 9th European Congress on Epileptology in Epilepsia, Jun. 27-Jul. 1, 2010, Rhodes, Greece, vol. 51, Suppl. 4, 2 pages.
Gil-Nagel et al., "An investigation of the effect of eslicarbazepine acetate on cardiac repolarization: A pooled analysis of over-read electrocardiograms from three doubleblind phase III clinical studies", 9th European Congress on Epileptology in Epilepsia, Jun. 27-Jul. 1, 2010, Rhodes, Greece, vol. 51, Suppl. 4, 2 pages.

(56) References Cited

OTHER PUBLICATIONS

Maia et al., "Seizure freedom and patient retention with adjunctive eslicarbazepine acetate therapy in adults with -efractory partial seizures during three randomized, doubleblind, placebo-controlled trials with 1-year, open-label extensions", 9th European Congress on Epileptology in Epilepsia, Jun. 27-Jul. 1, 2010, Rhodes, Greece, vol. 51, Suppl. 4, 2 pages.

Pinette et al., "The incidence of cognitive adverse events related to eslicarbazepine acetate: An integrated analysis of hree double-blind studies of eslicarbazepine acetate as adjunctive treatment for partial-onset seizures", Journal of the American Epilepsy Society, Dec. 3-7 2010, San Antonio, TX, USA, Article 1.287, vol. 11, Suppl. 1, 3 pages.

Versavel et al., "An exploratory subgroup analysis of the safety and efficacy of eslicarbazepine acetate administered once daily as concomitant treatment to levetiracetam: An integrated analysis of two Phase III studies", Journal of the American Epilepsy Society, Dec. 3-7 2010, San Antonio, TX, USA, Article 1.289, vol. 11, Suppl. 1, 3 pages.

Zummo et al., "An evaluation of the effect of eslicarbazepine acetate on weight, glucose, and lipids: An integrated analysis of three double-blind phase III clinical studies", Journal of the American Epilepsy Society, Dec. 3-7 2010, San Antonio, TX, USA, Article 2.153, vol. 11, Suppl. 1, 2 pages.

Versavel et al., "Efficacy of eslicarbazepine acetate by type of concomitantly used AEDs: An exploratory integrated analysis of two phase III studies", Journal of the American Epilepsy Society, Dec. 2-6 2011, Baltimore, MD, USA, Article 2.253, vol. 12, Suppl. 1, 2 pages.

Zummo et al., "Safety of eslicarbazepine acetate by type of concomitantly used aeds: an exploratory integrated analysis of two phase III studies", Journal of the American Epilepsy Society, Dec. 2-6 2011, Baltimore, MD, USA, Article 2.254, vol. 12, Suppl. 1, 2 pages.

Blum et al., "The incidence of cognitive adverse events related to eslicarbazepine acetate: an integrated analysis", Journal of the American Epilepsy Society, Dec. 2-6 2011, Baltimore, MD, USA, Article 2.256, vol. 12, Suppl. 1, 2 pages.

Sperling et al., "An investigation of the incidence and time to onset of adverse events associated with eslicarbazepine acetate adjunct treatment: an integrated analysis of two double blind placebo-controlled trials", Journal of the American Epilepsy Society, Dec. 2-6, 2011, Baltimore, MD, USA, Article 2.257, vol. 12, Suppl. 1, 3 pages.

Passarell et al., "Exposure-response analysis of eslicarbazepine acetate adjunctive treatment of patients with partial-onset seizures", Journal of Clinical Pharmacology & Therapeutics, 2011, vol. 89, Suppl. 1, 1 page.

Versavel et al., "Efficacy of eslicarbazepine acetate by type of concomitantly used AEDs: an exploratory integrated analysis of two phase III studies", 65th Annual American Epilepsy Society Meeting, Dec. 2-6, 2011, Baltimore, MD, USA, 1 page.

Sperling et al., "An investigation of the incidence and time to onset of adverse events associated with eslicarbazepine acetate adjunct treatment: An integrated analysis of two double-blind placebo-controlled trials", 65th Annual American Epilepsy Society Meeting, Dec. 2-6, 2011, Baltimore, MD, USA, 1 page.

Blum et al., "The incidence of cognitive adverse events related to eslicarbazepine acetate: An integrated analysis", 65th Annual American Epilepsy Society Meeting, Dec. 2-6, 2011, Baltimore, MD, USA, 1 page.

Grinnell et al., "Safety of eslicarbazepine acetate by type of concomitantly used AEDs: An exploratory integrated analysis of two phase III studies", 65th Annual American Epilepsy Society Meeting, Dec. 2-6, 2011, Baltimore, MD, USA, 1 page.

Lopes-Lima et al., "The metabolic profile of patients with epilepsy treated with eslicarbazepine acetate: Integrated analyses of plasma lipid and glucose parameters, and distribution of related adverse events in placebo-controlled phase III clinical studies", 29th International Epilepsy Congress, Aug. 28-Sep. 1, 2011, 1 page.

Gil-Nagel et al., "An integrated data analysis from three placebo-controlled clinical studies on over-read electrocardiograms of epileptic patients treated with eslicarbazepine acetate: Are there any effects on cardiac impulse ransmission?", 29th International Epilepsy Congress, Aug. 28-Sep. 1, 2011, 1 page.

Perucca et al., "In healthy subjects, concomitant use of carbamazepine with eslicarbazepine acetate can decrease exposure to eslicarbazepine: Lack of pharmacokinetic effects of ESL on CBZ and its 10,11-epoxide metabolite cofirms findings from clinical phase III studies", 29th International Epilepsy Congress, Aug. 28-Sep. 1, 2011, 1 page.

Guekht et al., "Incidence of adverse events in relation to starting-dose and titration regimen of eslicarbazepine acetate as add-on treatment in patients with partial-onset seizures", 29th International Epilepsy Congress, Aug. 28-Sep. 1, 2011, 1 page.

Falcao et al., "Steady-state pharmacokinetics of eslicarbazepine acetate: Integrated pool analyses from three double-blind phase Iii clinical studies", 29th International Epilepsy Congress, Aug. 28-Sep. 1, 2011, 1 page.

Bialer et al., "To what extent can eslicarbazepine acetate influence the plasma levels of combined antiepileptic drugs? An evaluation based on three double-blind phase III clinical studies", 29th International Epilepsy Congress, Aug. 28-Sep. 1, 2011, 1 page.

Capovilla et al., "Methods used to evaluate cognitive effects of eslicarbazepine acetate add-on therapy in epileptic ahildren of age 6-16: the design of a placebo-controlled clinical trial", 29th International Epilepsy Congress, Aug. 28-Sep. 1, 2011, 1 page.

Pinto et al., "A clinical study method used to evaluate the efficacy and safety of novel antiepileptic drug eslicarbazepine acetate in epileptic children with partial-onset seizures", 29th International Epilepsy Congress, Aug. 28-Sep. 1, 2011, 1 page.

Trinka et al., "The design of a double-dummy, active-controlled, multi-national Phase-III non-inferiority study in 900 adult patients with partial-onset seizures: eslicarbazepine acetate versus controlled-release carbamazepine in monotherapy", 29th International Epilepsy Congress, Aug. 28-Sep. 1, 2011, 1 page.

Nunes et al., "The design of a phase III clinical study of eslicarbazepine acetate in elderly patients with partial-onset seizures in epilepsy", 29th International Epilepsy Congress, Aug. 28-Sep. 1, 2011, 1 page.

Kharidia et al., "Exposure-response analysis of eslicarbazepine acetate as adjunctive treatment of patients with partial-onset seizures", American College of Clinical Pharmacy Annual Meeting, Oct. 16-19, 2011, 1 page.

Chang et al., "Eslicarbazepine acetate add-on for drug-resistant partial epilepsy (Review)", The Cochrane Library, 2011, Issue 12, pp. 1-38.

Chung et al., "New and emerging treatments for epilepsy: Review of clinical studies of lacosamide, eslicarbazepine acetate, ezogabine, rufinamide, perampanel, and electrical stimulation therapy", Journal of Epilepsy Research, 2011, vol. 1, No. 2, pp. 35-46.

Fattore et al. "Novel medications for epilepsy", Drugs, 2011, vol. 71, issue 16, pp. 2151-2178.

Perucca et al., "Pharmacokinetics of eslicarbazepine acetate at steady-state in adults with partial-onset seizures", Epilepsy Research, 2011, pp. 1-8.

Prunetti et al., "New and forthcoming anti-epileptic drugs", Current Opinion in Neurology, 2011, vol. 24, pp. 159-164.

Singh et al., "A Review of eslicarbazepine acetate for the adjunctive treatment of partial-onset epilepsy", Journal of central Nervous System Disease, 2011, Issue 3, pp. 179-187.

Steinhoff et al., "Abrupt switch from extended-release oxcarbazepine to eslicarbazepine acetate", Nervenarzt, 2011, vol. 82, Issue 6, pp. 764-767, including English summary at p. 765.

Stephen et al., "Pharmacotherapy of epilepsy newly approved and developmental agents", CNS Drugs, 2011, vol. 25, Issue 2, pp. 89-107.

Halasz et al., "An evaluation of efficacy and safety of adjunctive eslicarbazepine acetate in three double-blind clinical studies on patients with partial-onset seizures unsatisfactorily treated with carbamazepine", Epilepsia, 2011, vol. 52, Suppl. 6, 3 pages.

(56) References Cited

OTHER PUBLICATIONS

Guekht et al., "Incidence of adverse events in relation to starting dose and titration regimen of eslicarbazepine acetate as add-on treatment in patients with partial-onset seizures", Epilepsia, 2011, vol. 52, Suppl. 6, 2 pages.
Falcao et al., "Steady-state pharmacokinetics of eslicarbazepine acetate: Integrated pool analyses from three double-blind phase III clinical studies", Epilepsia, 2011, vol. 52, Suppl. 6, 3 pages.
Bialer et al., "To what extent can eslicarbazepine acetate influence the plasma levels of combined antiepileptic drugs? An evaluation based on three double-blind phase III clinical studies", Epilepsia, 2011, vol. 52, Suppl. 6, 2 pages.
Capovilla et al., "Methods used to evaluate cognitive effects of eslicarbazepine acetate add-on therapy in epileptic childre, of age 6-16: The design of a placebo-controlled clinical trial", Epilepsia, 2011, vol. 52, Suppl. 6, 2 pages.
Trinka et al., "The design of a double-dummy, active controlled, multinational phase-III noninferiority trial in 900 patients with partialonset seizures: Eslicarbazepine acetate versus controlled-release carbamazepine in monotherapy", Epilepsia, 2011, vol. 52, Suppl. 6, 3 pages.
Nunes et al., "The design of a phase III clinical study of eslicarbazepine acetate in elderly patients with partial-onset seizures in epilepsy", Epilepsia, 2011, vol. 52, Suppl. 6, 2 pages.
Perucca et al., "In healthy subjects, concomitant use of carbamazepine with eslicarbazepine acetate can decrease exposure to eslicarbazepine: Lack of pharmacokinetic effects of eslicarbazepine acetate on carbamazepine and its 10,11-epoxide metabolite confirms findings from clinical phase III studies", Epilepsia, 2011, vol. 52, Suppl. 6, 2 pages.
Loureiro et al., "One year experience with eslicarbazepine acetate on a community hospital in porto, portugal", Epilepsia, 2011, vol. 52, Suppl. 6, 2 pages.
Oehl et al., "A comparison of sodium levels in patients switched from oxcarbazepine to eslicarbazepine acetate", Epilepsia, 2011, vol. 52, Suppl. 6, 2 pages.
Blum et al., "The design of a double-blind, randomized, historical control study of the safety and efficacy of aslicarbazepine acetate monotherapy in subjects with partial epilepsy not well controlled by current antiepileptic drugs", Epilepsia, 2011, vol. 52, Suppl. 6, 2 pages.
Buschmann et al., "Effects of eslicarbazepine on cognition in patients with focal epilepsy", Epilepsia, 2011, vol. 52, Suppl. 6, 3 pages.
Pinto et al., "A clinical study method used to evaluate the efficacy and safety of novel antiepileptic drug eslicarbazepine acetate in epileptic children with partial-onset seizures", Epilepsia, 2011, vol. 52, Suppl. 6, 2 pages.
Gil-Nagel et al., "An integrated data analysis from three placebo-controlled clinical studies on over-read electrocardiograms of epileptic patients treated with eslicarbazepine acetate: Are there any effects on cardiac impulse transmission?", Epilepsia, 2011, vol. 52, Suppl. 6, 2 pages.
Philips et al., "Economic evaluation of adjunctive eslicarbazepine acetate in patients with refractory partial-onset seizures", Epilepsia, 2011, vol. 52, Suppl. 6, 2 pages.
Lopes-Lima et al., "The metabolic profile of patients with epilepsy treated with eslicarbazepine acetate: Integrated analyses of plasma lipid and glucose parameters, and distribution of related adverse events in placebo-controlled phase III clinical studies", Epilepsia, 2011, vol. 52, Suppl. 6, 3 pages.
Holtkamp et al., "Design of the EPOS study: An open-label, multicentre, non-interventional study to evaluate eslicarbazepine acetate as adjunctive treatment to one baseline antiepileptic drug in adults with partial-onset seizures", 10th European Congress on Epileptology, London, UK, Sep. 30-Oct. 4, 2012, 1 page.
Moreira et al., "Design of a phase III, double-blind, double-dummy, active-controlled, multi-national non-inferiority monotherapy study of eslicarbazepine acetate versus controlled-release carbamazepine in adults with partial-onset seizures", 10th European Congress on Epileptology, London, UK, Sep. 30-Oct. 4, 2012, 1 page.
Mota et al., "A clinical study method used to evaluate the efficacy and safety of the novel antiepileptic drug aslicarbazepine acetate in children with partial-onset seizures", 10th European Congress on Epileptology, London, UK, Sep. 30-Oct. 4, 2012, 1 page.
Bialer et al., "Effect of eslicarbazepine acetate on plasma levels of concomitant antiepileptic drugs: A population pharmacokinetics evaluation based on double-blind phase III clinical studies", 10th European Congress on Epileptology, London, UK, Sep. 30-Oct. 4, 2012, 1 page.
Eiger et al., "A post-hoc analysis of the time to onset of efficacy after initiation of eslicarbazepine acetate as adjunctive herapy in adult patients with refractory partial-onset seizures", 66th American Epilepsy Society Annual Meeting, Nov. 30-Dec. 4, 2012, San Diego, CA, 1 page.
Gil-Nagel et al., "A post-hoc exploratory analysis of the effect of eslicarbazepine acetate as adjunctive treatment in adult patients with partial-onset seizures refractory to carbamazepine", 66th American Epilepsy Society Annual Meeting, Nov. 30-Dec. 4, 2012, San Diego, CA, 1 page.
Carreno et al., "A post-hoc exploratory analysis of the effect of eslicarbazepine acetate as adjunctive treatment in adult patients with partial-onset seizures and comorbid clinically relevant depressive symptoms", 66th American Epilepsy Society Annual Meeting, Nov. 30-Dec. 4, 2012, San Diego, CA, 1 page.
Bialer et al., "Pharmacokinetics and drug interactions of eslicarbazepine acetate", Epilepsia, 2012, pp. 1-12.
Bialer et al., "Chemical properties of antiepileptic drugs (AEDs)", Advanced Drug Delivery Reviews, 2012, pp. 387-895.
Falcao et al., "Pharmacokinetics, drug interactions and exposure-response relationship of eslicarbazepine acetate in adult patients with partial-onset seizures", CNS Drugs, 2012, vol. 26, Issue 1, pp. 79-91.
Mauri-Llerda, "Eslicarbazepine acetate: A novel therapeutic alternative in the treatment of focal seizures", Rev Neural, 2012, vol. 54., No. 9, pp. 551-555, including English summary at p. 555.
Marco Mula, "Recent and future antiepileptic drugs and their impact on cognition: What can we expect?", Expert Rev leurother, 2012, vol. 12, Issue 6, pp. 667-671.
Patsalos et al., "Pharmacotherapy of the thirdgeneration AEDs: Lacosamide, retigabine and eslicarbazepine acetate", Expert Opinion on Pharmacotherapy, 2012, vol. 13, Issue 5, pp. 699-715.
Correia et al., "One year follow-up experience with eslicarbazepine acetate (Zebinix ) in a tertiary hospital in oporto, portugal", 10th European Congress on Epileptology in Epilepsia, Sep. 30-Oct. 4, 2012, London, UK, vol. 53, Suppl. 5, 2 pages.
Mota et al., "A clinical study method used to evaluate the efficacy and safety of novel antiepileptic drug eslicarbazepine acetate in epileptic children with partial-onset seizures", 10th European Congress on Epileptology in Epilepsia, Sep. 30-Oct. 4, 2012, London, UK, vol. 53, Suppl. 5, 2 pages.
Moreira et al., "Design of a phase Hi, double-dummy, active-controlled, multi-national non-inferiority monotherapy trial of eslicarbazepine acetate versus controlled-release carbamazepine in adults with partial-onset seizures", 10th European Congress on Epileptology in Epilepsia, Sep. 30-Oct. 4, 2012, London, UK, vol. 53, Suppl. 5, 2 pages.
Bialer et al., "Eslicarbazepine acetate and plasma levels of combined antiepileptic drugs: A population pharmacokinetics evaluation based on double-blind phase III clinical studies", 10th European Congress on Epileptology in Epilepsia, Sep. 30-Oct. 4, 2012, London, UK, vol. 53, Suppl. 5, 3 pages.
Fraile et al., "Eslicarbazepine use in mentally retarded and refractory epileptic patients", 10th European Congress on Epileptology in Epilepsia, Sep. 30-Oct. 4, 2012, London, UK, vol. 53, Suppl. 5, 2 pages.
Holtkamp et al., "Design of the EPOS study: An open-label, multicentre, non-interventional study to evaluate eslicarbazepine acetate as adjunctive treatment to one baseline antiepileptic drug in adults with partial-onset seizures", 10th European Congress on Epileptology in Epilepsia, Sep. 30-Oct. 4, 2012, London, UK, vol. 53, Suppl. 5, 2 pages.

(56) References Cited

OTHER PUBLICATIONS

Elger et al., "A post-hoc analysis of the time to onset of efficacy after initiation of eslicarbazepine acetate as adjunctive herapy in adult patients with refractory partial-onset seizures", Journal of the American Epilepsy Society, Nov. 30-Dec. 4, 2012, San Diego, CA, USA, Article 1.230, 3 pages.
Rocamora et al., "Prospective post-authorization observational study of eslicarbazepine (ESL) in the treatment of pharmacoresistant epilepsies", Journal of the American Epilepsy Society, Nov. 30-Dec. 4, 2012, San Diego, CA, USA, Article 2.200, 3 pages.
Freitas et al., "Safety profile of eslicarbazepine acetate: Two year experience in a tertiary hospital", Journal of the American Epilepsy Society, Nov. 30-Dec. 4, 2012, San Diego, CA, USA, Article 2.201, 2 pages.
Gil-Nagel et al., "A post-hoc exploratory analysis of the effect of eslicarbazepine acetate as adjunctive treatment in adult patients with partialonset seizures refractory to carbamazepine", Journal of the American Epilepsy Society, Nov. 30-Dec. 4, 2012, San Diego, CA, USA, Article 3.228, 3 pages.
Carreno et al., "A post-hoc exploratory analysis of the effect of eslicarbazepine acetate as adjunctive treatment in adult patients with partialonset seizures and comorbid clinically relevant depressive symptoms", Journal of the American Epilepsy Society, Nov. 30-Dec. 4, 2012, San Diego, CA, USA, Article 3.229, 3 pages.
Damodaran et al., "Clinical effectiveness of eslicarbazepine acetate (Zebinex) as an add-on therapy in localization related epilepsy over 12 months", Journal of the American Epilepsy Society, Nov. 30-Dec. 4, 2012, San Diego, CA, USA, Article 3.247, 3 pages.
Hofler et al., "Tolerability of overnight switch from oxcarbazepine to eslicarbazepine acetate", Journal of the American Epilepsy Society, Nov. 30-Dec. 4, 2012, San Diego, CA, USA, Article 3.258, 2 pages.
Neves et al., "Efficacy and tolerability of adjunctive eslicarbazepine acetate in adults with drugresistant focal epilepsies in a portuguese epilepsy center", Journal of the American Epilepsy Society, Nov. 30-Dec. 4, 2012, San Diego, CA, USA, Article 3.264, 2 pages.
Gao et al., "Clinical efficacy and safety of the newer antiepileptic drugs as adjunctive treatment in adults with refractory partial-onset epilepsy: A meta-analysis of randomized placebo-controlled trials", Epilepsy Research, 2013, vol. 103, pp. 31-44.
Gil-Nagel et al., "Efficacy and safety of eslicarbazepine acetate as add-on treatment in patients with focal-onset seizures: Integrated analysis of pooled data from double-blind phase III clinical studies", Epilepsia, 2013, vol. 54, No. 1, pp. 98-107.
Hufnagel et al., "Long-term safety and efficacy of eslicarbazepine acetate as adjunctive therapy in the treatment of partial-onset seizures in adults with epilepsy: Results of a 1-year open-label extension study", Epilepsy Research, 2012, pp. 1-8.
Massot et al., "Post-authorisation study of eslicarbazepine as treatment for drug-resistant epilepsy: Preliminary results", Neurologia, 2013, pp. 1-8, including English summary on p. 2.
Serrano-Castro et al., "Eslicarbazepine acetate in clinical practice. Efficacy and safety results", Rev Neural, 2013, vol. 56, Issue 6, pp. 309-314, including English summary on p. 314.
Siniscalchi et al., "A review on antiepileptic drugs-dependent fatigue:Pathophysiological mechanisms and incidence", European Journal of Pharmacology, 2013, pp. 10-16.
Zaccara et al., "Neurological adverse events of new generation sodium blocker antiepileptic drugs. Meta-analysis of randomized, double-blinded studies with eslicarbazepine acetate, lacosamide and oxcarbazepine", Seizure, 2013, pp. 1-9.
Sperling et al., "Conversion to monotherapy with eslicarbazepine acetate in adults with partial-onset seizures: Results Df a North-American study", 67th Annual American Epilepsy Society Meeting, Dec. 6-10, 2013, Washington, DC, USA, Article 3.293, 1 page.
Pazdera et al., "Conversion to monotherapy with eslicarbazepine acetate in adults with partial-onset seizures", 67th Annual American Epilepsy Society Meeting, Dec. 6-10, 2013, Washington, DC, USA, Article 1.228, 1 page.
Sperling et al., "Adjunctive eslicarbazepine acetate in patients with refractory partial-onset seizures: Efficacy results of a 12 week randomized placebo-controlled study", 67th Annual American Epilepsy Society Meeting, Dec. 6-10, 2013, Washington, DC, USA, Article 3.210, 1 page.
Abou-Khalil et al., "Eslicarbazepine acetate as adjunctive therapy in patients with refractory partial-onset seizures: Safety results of a 12-week randomized placebo-controlled study", 67th Annual American Epilepsy Society Meeting, Dec. 6-10, 2013, Washington, DC, USA, Article 2.128, 1 page.
Bollu et al., "Impact of treatment-associated adverse events on healthcare resource utilization and costs among patients with partial-onset seizures: A longitudinal analysis", 67th Annual American Epilepsy Society Meeting, Dec. 6-10, 2013, Washington, DC, USA, Article 2.146, 1 page.
Velez et al., "The economic burden of central nervous system events among patients with partial-onset seizures reated with antiepileptic drugs", 67th Annual American Epilepsy Society Meeting, Dec. 6-10, 2013, Washington, DC, USA, Article 2.147, 1 page.
Velez et al., "Healthcare utilization among patients with uncontrolled epilepsy: A retrospective study in a commercially nsured US population", 67th Annual American Epilepsy Society Meeting, Dec. 6-10, 2013, Washington, DC, USA, Article 2.230, 1 page.
Petrilla et al., "Resource utilization among epilepsy patients with and without breakthrough seizures in a US managed aare population", 67th Annual American Epilepsy Society Meeting, Dec. 6-10, 2013, Washington, DC, USA, Article 2.137, 1 page.
Blum et al., "Effects of eslicarbazepine acetate on serum lipids in statin users and non users: Pooled analysis of placebo-controlled trials", 67th Annual American Epilepsy Society Meeting, Dec. 6-10, 2013, Washington, DC, USA, Article 2.139, 1 page.
Biton et al., "Efficacy of eslicarbazepine acetate in patients with refractory partial-onset seizures: A pooled analysis of Three Phase III controlled studies", 67th Annual American Epilepsy Society Meeting, Dec. 6-10, 2013, Washington, DC, USA, Article 2.127, 1 page.
Rogin et al., "Eslicarbazepine acetate as adjunctive treatment for refractory partial-onset seizures: Pooled analysis of safety data from three Phase III controlled trials", 67th Annual American Epilepsy Society Meeting, Dec. 6-10, 2013, Washington, DC, USA, Article 2.126, 1 page.
Jacobson et al., "Effects of concomitant antiepileptic drugs on eslicarbazepine acetate: A population pharmacokinetic analysis", 67th Annual American Epilepsy Society Meeting, Dec. 6-10, 2013, Washington, DC, USA, Article 3.202, 1 page.
Krauss et al., "Adverse event profile of eslicarbazepine acetate according to dose titration in Phase III controlled studies of patients with refractory partial-onset seizures", 67th Annual American Epilepsy Society Meeting, Dec. 5-10, 2013, Washington, DC, USA, Article 3.208, 1 page.
Carreno et al., "A post-hoc exploratory analysis of the effect of eslicarbazepine acetate as adjunctive treatment in adult patients with partial-onset seizures and comorbid clinically relevant depressive symptoms", 30th International Epilepsy congress, Jun. 23-27, 2013, Montreal, Canada, 1 page.
Gil-Nagel et al., "A pooled analysis of the efficacy of approved dosages of eslicarbazepine acetate as adjunctive therapy of adult patients with partial-onset seizures up to one year of follow-up", 23rd Meeting of the European Neurological Society, Jun. 8-11, 2013, Barcelona, Spain, 1 page.
Elger et al., "A pooled analysis of the tolerability of approved dosages of eslicarbazepine acetate as adjunctive therapy of adult patients with partial-onset seizures up to one year of follow-up", 23rd Meeting of the European Neurological Society, Jun. 8-11, 2013, Barcelona, Spain, 1 page.
Elger et al., "A pooled analysis of the tolerability of approved dosages of eslicarbazepine acetate as adjunctive therapy of adult patients with partial-onset seizures up to one year of follow-up", XXI World Congress of Neurology, Sep. 21-26, 2013, Vienna, Austria, 1 page.
Carreno et al., "A post-hoc exploratory analysis of the effect of eslicarbazepine acetate as adjunctive therapy in adult patients with partial-onset seizures and comorbid clinically relevant depressive symptoms", 30th International Epilepsy congress in Epilepsia, Jun. 23-27, 2013, Montreal, Canada, vol. 54, Suppl. 3, 2 pages.

(56) References Cited

OTHER PUBLICATIONS

Dias Correia et al., "Two-year clinical experience with eslicarbazepine acetate in a tertiary hospital in oporto, portugal", 30th International Epilepsy Congress in Epilepsia, Jun. 23-27, 2013, Montreal, Canada, vol. 54, Suppl. 3, 2 pages.
Pazdera et al., "Conversion to monotherapy with eslicarbazepine acetate in adults with partial-onset seizures", Epilepsy Currents, 2013, vol. 14, No. s1, Article 1.228, 2 pages.
Serratosa et al., "An spanish collection of patients with eslicarbazepine in clinical practice", Epilepsy Currents, 2013, vol. 14, No. s1, Article 1.234, 2 pages.
Rogin et al., "Eslicarbazepine acetate as adjunctive treatment for refractory partial-onset seizures: Pooled analysis of safety data from three Phase III controlled trials", Epilepsy Currents, 2013, vol. 14, No. s1, Article 2.126, 2 pages.
Biton et al., "Efficacy of eslicarbazepine acetate in patients with refractory partial onset seizures: A pooled analysis of three Phase III controlled studies", Epilepsy Currents, 2013, vol. 14, No. s1, Article 2.127, 3 pages.
Abou-Khalil et al., "Eslicarbazepine acetate as adjunctive therapy in patients with refractory partialonset seizures: Safety results of a 12-week randomized placebo-controlled study", Epilepsy Currents, 2013, vol. 14, No. s1, Article 2.128, 3 pages.
Blum et al., "Effects of eslicarbazepine acetate on serum lipids in statin users and non-users: Pooled analysis of placebo-controlled trials", Epilepsy Currents, 2013, vol. 14, No. sl, Article 2.139, 3 pages.
Jacobson et al., "Interactions between concomitant antiepileptic drugs and eslicarbazepine acetate: A population pharmacokinetic analysis", Epilepsy Currents, 2013, vol. 14, No. s1, Article 3.202, 2 pages.
Krauss et al., "Adverse event profile of eslicarbazepine acetate during dose titration in Phase III controlled studies of patients with refractory partial-onset seizures", Epilepsy Currents, 2013, vol. 14, No. s1, Article 3.208, 3 pages.
Sperling et al., "Adjunctive eslicarbazepine acetate in patients with refractory partial-onset seizures: Efficacy results of a 12 week randomized placebo-controlled study", Epilepsy Currents, 2013, vol. 14, No. s1, Article 3.210, 2 pages.
Sperling et al., "Conversion to monotherapy with eslicarbazepine acetate in adults with partial-onset seizures-results of a northamerican study", Epilepsy Currents, 2013, vol. 14, No. s1, Article 3.293, 3 pages.
Arenga et al., "His tics have changed a lot": beyond Gilles de la Tourette syndrome, J. Neural, Jun. 8-11, 2013, Barcelona, Spain, vol. 260, Suppl. 1, 2 pages.
Elger et al., "A pooled analysis of the tolerability of approved dosages of eslicarbazepine acetate as adjunctive therapy for adult patients with partial-onset seizures up to 1 year of follow-up", J. Neural, Jun. 8-11, 2013, Barcelona, Spain, vol. 260, Suppl. 1, 2 pages.
Gil-Nagel et al., "A pooled analysis of the efficacy of approved dosages of eslicarbazepine acetate as adjunctive therapy for adult patients with partial-onset seizures up to 1 year of follow-up", J. Neural, Jun. 8-11, 2013, Barcelona, Spain, vol. 260, Suppl. 1, 2 pages.
Gil-Nagel et al., "Efficacy of eslicarbazepine acetate as adjunctive therapy of adult patients with partial-onset seizures up to one year of follow-up", Journal of the Neurological Sciences, 2013, No. 1277, 2 pages.
Abou-Khalil et al., "Eslicarbazepine acetate monotherapy: a population pharmacokinetic analysis", 68th Annual American Epilepsy Society Meeting, Dec. 5-9, 2014, Seattle, WA, USA, Article 1.321, 1 page.
Andermann et al., "Eslicarbazepine acetate as adjunctive therapy for refractory partial-onset seizures: analysis of cognitive adverse events", 68th Annual American Epilepsy Society Meeting, Dec. 5-9, 2014, Seattle, WA, USA, Article 1.317, 1 page.
Benbadis et al., "Incidence of seizure exacerbation and seizure-related adverse events during adjunctive treatment with eslicarbazepine acetate: a pooled analysis of three Phase III controlled trials", 68th Annual American Epilepsy Society Meeting, Dec. 5-9, 2014, Seattle, WA, USA, Article 1.322, 1 page.
Biton et al., "Analysis of psychiatric adverse events in three Phase III controlled trials of eslicarbazepine acetate as adjunctive therapy for refractory partial-onset seizures", 68th Annual American Epilepsy Society Meeting, Dec. 5-9, 2014, Seattle, WA, USA, Aricle 2.278, 1 page.
Blum et al., "Hepatic safety of eslicarbazepine acetate: summary of five Phase II and three Phase III adjunctive trials", 68th Annual American Epilepsy Society Meeting, Dec. 5-9, 2014, Seattle, WA, USA, Article 1.316, 1 page.
Correia et al., "Two-year follow-up with eslicarbazepine acetate: a consecutive, retrospective, observational study", Epilepsy Research, 2014, pp. 1-7.
Cramer et al., "Seizure severity among subjects with refractory partial-onset seizures: analysis of the Seizure Severity Duestionnaire in a Phase III trial of eslicarbazepine acetate", 68th Annual American Epilepsy Society Meeting, Dec. 5-9, 2014, Seattle, WA, USA, Article 1.287, 1 page.
De et al., "A systematic review and network meta-analyasis of eslicarbazepine acetate and other recently-approved antiepileptic drugs for adjunctive treatment of partial-onset seizures in adults", 68th Annual American Epilepsy Society Meeting, Dec. 5-9, 2014, Seattle, WA, USA, Article 1.342, 1 page.
Divino et al., "Healthcare resource utilization and costs of immediate versus delayed second-line treatment initiation among patients with epilepsy", 68th Annual American Epilepsy Society Meeting, Dec. 5-9, 2014, Seattle, WA, USA, Article 2.044, 1 page.
Holtkamp et al., "Eslicarbazepine acetate as add-on treatment to antiepileptic monotherapy in adults with partial-onset seizures: Real-world data on retention, dosing, Patient reported seizure outcome and safety from an interim analysis of the open-label non-interventional study EPOS", 11th European Congress on Epileptology , Jun. 29-Jul. 4, 2014, 1 page.
Gama et al., "Safety of eslicarbazepine acetate after 4 years of post-marketing experience in Europe", 11th European Congress on Epileptology, Jun. 29-Jul. 4, 2014, 1 page.
Holtkamp et al., "Eslicarbazepine acetate as add-on treatment to antiepileptic monotherapy in adults with partial-onset seizures: Real-world data on retention, dosing, Patient reported seizure outcome and safety from an interim analysis of the open-label Non-interventional study EPOS", Eslicarbazepine Acetate in Partial-Onset Seizures, Poster Nr.p140, 11th European Congress on Epileptology , Jun. 29-Jul. 4, 2014, 3 pages.
Fakhoury et al., "Relationship between eslicarbazepine exposure and safety endpoints for eslicarbazepine acetate monotherapy", 68th Annual American Epilepsy Society Meeting, Dec. 5-9, 2014, Seattle, WA, USA, Article 1.312, 1 page.
Harvey et al., "Relationship between eslicarbazepine exposure and efficacy of eslicarbazepine acetate adjunctive therapy", 68th Annual American Epilepsy Society Meeting, Dec. 5-9, 2014, Seattle, WA, USA, Article 1.319, 1 page.
Keating, "Eslicarbazeine Acetate: A Review of Its Use as Adjunctive Therapy in Refractory Partial-Onset Seizures", CNS Drugs, 2014, vol. 28, pp. 583-600.
Krauss et al., "Improvement in seizure control during conversion to eslicarbazepine acetate monotherapy: a pooled analysis of two trials in adults with refractory partial-onset seizures", 68th Annual American Epilepsy Society Meeting, Dec. 5-9, 2014, Seattle, WA, USA, Article 2.292, 1 page.
Massot et al., "Cutaneous adverse drug reaction type erythema multiforme major induced by eslicarbazepine", Journal of Pharmacology and Pharmacotherapeutics, Oct.-Dec. 2014, vol. 5, Issue 4, pp. 271-274.
O'Day et al., "Cost-effectiveness of eslicarbazepine acetate in refractory partial-onset epilepsy", 68th Annual American Epilepsy Society Meeting, Dec. 5-9, 2014, Seattle, WA, USA, Article 1.344, 1 page.

(56) References Cited

OTHER PUBLICATIONS

Pazdera et al., "Eslicarbazepine acetate monotherapy in adults with partial-onset seizures: a pooled analysis of two randomized, double-blind studies with use of a historical control", 68th Annual American Epilepsy Society Meeting, Dec. 5-9, 2014, Seattle, WA, USA, Article 1.318, 1 page.

Penovich et al., "Relationship between eslicarbazepine exposure and safety endpoints for eslicarbazepine acetate adjunctive therapy", 68th Annual American Epilepsy Society Meeting, Dec. 5-9, 2014, Seattle, WA, USA, Article 1.320, 1 page.

Rogin et al., "Relationship between exposure and efficacy of eslicarbazepine acetate monotherapy", 68th Annual American Epilepsy Society Meeting, Dec. 5-9, 2014, Seattle, WA, USA, Article 1.314, 1 page.

Rosenfeld et al., "Incidence of falls, fractures, and injuries with adjunctive eslicarbazepine acetate in patients with refractory partial-onset seizures: a pooled analysis of three placebo-controlled trials", 68th Annual American Epilepsy Society Meeting, Dec. 5-9, 2014, Seattle, WA, USA, Article 1.315, 1 page.

Schoedel et al., "Evaluation of physical dependence potential following abrupt discontinuation of adjunctive eslicarbazepine acetate: a pooled analysis of adverse events from 10 studies", 68th Annual American Epilepsy Society Meeting, Dec. 5-9, 2014, Seattle, WA, USA, Article 1.323, 1 page.

Sperling et al., "Long-term safety and efficacy of eslicarbazepine acetate monotherapy in adults with refractory partial-onset seizures: an open-label extension study", 68th Annual American Epilepsy Society Meeting, Dec. 5-9, 2014, Seattle, WA, USA, Article 2.290, 1 page.

Lima et al., "Preferred flavour of eslicarbazepine acetate oral suspension to paediatric epileptic subjects", 11th European Congress on Epileptology, Jun. 29-Jul. 4, 2014, 1 page.

Costa et al., "Safety and efficacy of eslicarbazepine acetate treatment in elderly patients", 11th European Congress on Epileptology, Jun. 29-Jul. 4, 2014, 1 page.

Velez et al., "Association between depressive symptoms and seizure response among subjects with refractory partial-onset seizures in clinical trials of eslicarbazepine acetate", 68th Annual American Epilepsy Society Meeting, Dec. 5-9, 2014, Seattle, WA, USA, Article 1.273, 1 page.

Verrotti et al., "Eslicarbazepine acetate: An update on efficacy and safety in epilepsy", Epilepsy Research, 2014, vol. 108, pp. 1-10.

Ben-Menachem et al., "Eslicarbazepine acetate", Epilepsy Research, 2009, vol. 83, pp. 15-17.

Elger et al., "Tolerability of eslicarbazepine acetate as adjunctive therapy of adult patients with partial-onset seizures up to one year of follow-up", Journal of the Neurological Sciences, 2013, No. 1279, 3 pages.

Keogh et al., "Safety and efficacy of eslicarbazepine acetate (Zebinix) in everyday clinical practice using a retrospective multicentre audit", Journal of the Neurological Sciences, 2013, No. 3219, 2 pages.

Boero et al., "Preliminary data on the efficacy and tolerability of eslicarbazepine as adjunctive therapy in patients with refractory partial epilepsy", 31st International Epilepsy Congress in Epilepsia, Sep. 5-9, 2015, Istanbul, Turkey, vol. 56, Suppl. 1, 2 pages.

Derambure et al., "Eslicarbazepine acetate as add-on to antiepileptic monotherapy in adults with partial-onset seizures (EPOS Study): Analysis by baseline antiepileptic drug", 31st International Epilepsy Congress in Epilepsia, Sep. 5-9, 2015, Istanbul, Turkey, vol. 56, Suppl. 1, 2 pages.

Holtkamp et al., "Real-world data on eslicarbazepine acetate as add-on treatment to antiepileptic monotherapy in adults with partial-onset seizures: The EPOS study", 31st International Epilepsy Congress in Epilepsia, Sep. 5-9, 2015, Istanbul, Turkey, vol. 56, Suppl. 1, 3 pages.

Nielsen et al., "Clinical experience with eslicarbazepine acetate with focus on elderly", 31st International Epilepsy Congress in Epilepsia, Sep. 5-9, 2015, Istanbul, Turkey, vol. 56, Suppl. 1, 2 pages.

Kerr et al., "Impact on quality of life and clinician-rated global improvement with eslicarbazepine acetate as add-on treatment to antiepileptic monotherapy in adults with partial-onset seizures", 31st International Epilepsy Congress in Epilepsia, Sep. 5-9, 2015, Istanbul, Turkey, vol. 56, Suppl. 1, 2 pages.

Landmark et al., "Eslicarbazepine acetate in refractory epilepsy: Extensive use of various polytherapies and clinical evaluation of the suggested reference range", 31st International Epilepsy Congress in Epilepsia, Sep. 5-9, 2015, Istanbul, Turkey, vol. 56, Suppl. 1, 1 page.

Fabrega et al., "Monotherapy experience with eslicarbazepine acetate", 31st International Epilepsy Congress in Epilepsia, Sep. 5-9, 2015, Istanbul, Turkey, vol. 56, Suppl. 1, 2 pages.

Poza et al., "Effect of eslicarbazepine acetate on serum lipid profile", 31st International Epilepsy Congress in Epilepsia, Sep. 5-9, 2015, Istanbul, Turkey, vol. 56, Suppl. 1, 2 pages.

Villegas-Martinez et al., "Vitamin D supplementation could be insufficient for osteoporosis prevention in persons with epilepsy on antiepileptic drugs", 31st International Epilepsy Congress in Epilepsia, Sep. 5-9, 2015, Istanbul, Turkey, vol. 56, Suppl. 1, 3 pages.

Losch et al., "Eslicarbazepine acetate as add-on treatment to antiepileptic monotherapy in adults with partial-onset seizures: German data of the EPOS study", European Journal of Neurology, 2015, vol. 22, Suppl. 1, 2 pages.

Holtkamp et al., "Eslicarbazepine acetate as add-on treatment to antiepileptic monotherapy in adults with partial-onset seizures: Real-world data from the EPOS study", European Journal of Neurology, 2015, vol. 22, Suppl. 1, 2 pages.

Lawthom et al., "Effectiveness of eslicarbazepine acetate as add-on treatment to antiepileptic monotherapy in adults with partial-onset seizures (EPOS study): Analysis by baseline antiepileptic drug", European Journal of Neurology, 2015, vol. 22, Suppl. 1, 2 pages.

Holtkamp et al., "Eslicarbazepine acetate as add on treatment to antiepileptic monotherapy in adults with partial-onset seizures: Real world data from the EPOS study", 1st European Academy of Neurology Congress, Jun. 20-23, 2015, Berlin, Germany, 12 pages.

Lawthom et al., "Effectivenes of eslicarbazepine acetate as add-on treatment to antiepileptic monotherapy in adults with partial-onset seizures (EPOS study): Analysis by baseline antiepileptic drug", 1st European Academy of geurology Congress, Jun. 20-23, 2015, Berlin, Germany, 1 page.

Losch et al., "Eslicarbazepine acetate as add-on treatment to antiepileptic monotherapy in adults with partial-onset seizures: German data of the EPOS study", 1st European Academy of Neurology Congress, Jun. 20-23, 2015, Berlin, Germany, 1 page.

Derambure et al., "Eslicarbazepine acetate as add-on to antiepileptic monotherapy in adults with partial-onset seizures (EPOS study): Analysis by baseline antiepileptic drug", 31st International Epilepsy Congress , Sep. 5-9, 2015, Istanbul, Turkey, 1 page.

Holtkamp et al., "Real-world data on eslicarbazepine acetate as add-on treatment to antiepileptic monotherapy in adults with partial-onset seizures: The EPOS study", 31st International Epilepsy Congress , Sep. 5-9, 2015, Istanbul, Turkey, 1 page.

Kerr et al., "Impact on quality of life and clinician-rated global improvement with eslicarbazepine acetate as add-on treatment to antiepileptic monotherapy in adults with partial-onset seizures", 31st International Epilepsy Congress, Sep. 5-9, 2015, Istanbul, Turkey, 1 page.

Banach et al., "Pharmacokinetic/pharmacodynamic evaluation of eslicarbazepine for the treatment of epilepsy", Expert Opinion on Drug Metabolism & Toxicology, 2015, vol. 11, Issue 4, pp. 639-648.

Martin J. Brodie, "Practical use of newer antiepileptic drugs as adjunctive therapy in focal epilepsy", CNS Drugs, Oct. 27, 2015, pp. 1-12.

Buoni et al., "Severe myoclonic epilepsy of infancy: Seizure reduction during adjunctive eslicarbazepine in two cases", Epilepsy & Behavior Case Reports, 2015, vol. 4, pp. 38-40.

Cacao et al., "SUNCT syndrome: A cohort of 15 Portuguese patients", Cephalalgia, 2015, pp. 1-5.

Cramer et al., "Severity and burden of partial-onset seizures in a phase III trial of eslicarbazepine acetate", Epilepsy & Behavior, 2015, vol. 53, pp. 149-153.

(56) References Cited

OTHER PUBLICATIONS

Doeser et al., "Targeting pharmacoresistant epilepsy and epileptogenesis with a dual-purpose antiepileptic drug", Brain, 2015, vol. 138, pp. 371-387.
Gupta et al., "Hyponatremia following esclicarbazepine therapy", Seizure, 2015, vol. 29, pp. 11-14.
Jacobson et al., "Efficacy and safety of conversion to monotherapy with eslicarbazepine acetate in adults with uncontrolled partial-onset seizures: A historical-control phase III study", BMC Neurology, 2015, vol. 15, pp. 1-13.
Holger Lerche, "New hope for the treatment of epilepsy", Brain, 2015, vol. 138, pp. 238-245.
Ley et al., "Assessing long-term effects of eslicarbazepine acetate on lipidmetabolism profile, sodium values and liver function tests", Epilepsy Research, 2015, vol. 115, pp. 147-152.
Peltola et al., "Practical guidance and considerations for transitioning patients from oxcarbazepine or carbamazepine to eslicarbazepine acetate-Expert opinion", Epilepsy & Behavior, 2015, vol. 50, pp. 46-49.
Rodrigo Rocamora, "A review of the efficacy and safety of eslicarbazepine acetate in the management of partial-onset seizures", Therapeutic Advances in Neurological Disorders, 2015, vol. 8, No. 4, pp. 178-186.
Sperling et al., "Efficacy and safety of conversion to monotherapy with eslicarbazepine acetate in adults with uncontrolled partial-onset seizures: A randomized historical-control phase III study based in North America", Epilepsia, 2015, pp. 1-10.
Zaccara et al., "Clinical utility of eslicarbazepine: Current evidence", Drug Design, Development and Therapy, Feb. 10, 2015, pp. 781-789.
Keogh et al., "Hyponatraemia with eslicarbazepine acetate (Zebinix) add in therapy in everyday clinical practice using a retrospective multicentre audit", 11th European Congress on Epileptology in Epilepsia, Jun. 29-Jul. 3, 2014, Stockholm, Sweden, vol. 55, Suppl. 2, 2 pages.
Camacho et al., "Effectiveness and tolerability of high dose eslicarbazepine", 11th European Congress on Epileptology in Epilepsia, Jun. 29-Jul. 3, 2014, Stockholm, Sweden, vol. 55, Suppl. 2, 2 pages.
Holtkamp et al., "Eslicarbazepine acetate as add-on treatment to antiepileptic monotherapy in adults with partial-onset seizures: Realworld data on retention, dosing, patient reported seizure outcome and safety from an interim analysis of the open-label noninterventional study EPOS", 11th European Congress on Epileptology in Epilepsia, Jun. 29-Jul. 3, 2014, Stockholm, Sweden, vol. 55, Suppl. 2, 2 pages.
Costa et al., "Safety and efficacy of eslicarbazepine acetate treatment in elderly patients", 11th European Congress on Epileptology in Epilepsia, Jun. 29-Jul. 3, 2014, Stockholm, Sweden, vol. 55, Suppl. 2, 2 pages.
Gama et al., "Safety of eslicarbazepine acetate after 4 years of post-marketing experience in europe", 11th European Congress on Epileptology in Epilepsia, Jun. 29-Jul. 3, 2014, Stockholm, Sweden, vol. 55, Suppl. 2, 2 pages.
Lima et al., "Preferred flavour of eslicarbazepine acetate oral suspension to paediatric epileptic subjects", 11th European Congress on Epileptology in Epilepsia, Jun. 29-Jul. 3, 2014, Stockholm, Sweden, vol. 55, Suppl. 2, 2 pages.
Ley Nacher et al., "Assessing long-term effects of eslicarbazepine on liver values and lipid metabolism profile", 11th European Congress on Epileptology in Epilepsia, Jun. 29-Jul. 3, 2014, Stockholm, Sweden, vol. 55, Suppl. 2, 2 pages.
Keogh et al., "Concomitant use of eslicarbazepine acetate (Zebinix) with carbamazepine in everyday clinical practice using a retrospective multicentre audit", 11th European Congress on Epileptology in Epilepsia, Jun. 29-Jul. 3, 2014, Stockholm, Sweden, vol. 55, Suppl. 2, 2 pages.
Landmark et al., "Clinical experience with therapeutic drug monitoring of eslicarbazepine acetate in norway", 11th European Congress on Epileptology in Epilepsia, Jun. 29-Jul. 3, 2014, Stockholm, Sweden, vol. 55, Suppl. 2, 1 page.
Rosenfeld et al., "Incidence of falls, fractures, and injuries with adjunctive eslicarbazepine acetate in patients with refractory partial-onset seizures: a pooled analysis of three placebo-controlled trials", 67th American Academy of Neurology Annual Meeting, Apr. 18-25, 2015, Washington, DC, USA, Article P4.277, 1 page.
Sunkaraneni et al., "Population pharmacokinetic evaluation and missed dose simulations for eslicarbazepine acetate monotherapy", 67th American Academy of Neurology Annual Meeting, Apr. 18-25, 2015, Washington, DC, USA, Article P4.258, 1 page.
Abou-Khalil et al., "Incidence of treatment-emergent adverse events in three Phase III studies of adjunctive eslicarbazepine acetate, in patients taking or not taking lamotrigine at baseline", 69th Annual American Epilepsy Society Meeting, Dec. 4-8, 2015, Philadelphia, PA, USA, Article P1.186, 1 page.
Bond et al., "Change in depressive symptoms among patients with refractory partial-onset seizures treated with eslicarbazepineacetate monotherapy: a pooled analysis of clinical trials", 69thAnnual American Epilepsy Society Meeting, Dec. 4-8, 2015, Philadelphia, PA, USA, Article 2.249, 1 page.
Anastassopoulos et al., "Predictors of 50% seizure frequency reduction among epilepsy patients with partial-onset seizures: a pooled analysis of Phase III clinical trials of adjunctive treatment with eslicarbazepineacetate", 69thAnnual American Epilepsy Society Meeting, Dec. 4-8, 2015, Philadelphia, PA, USA, Article 1.202, 1 page.
Cramer et al., "Quality of life improvement among patients with refractory partial-onset seizures: a clinical trial analysis of patients who responded to eslicarbazepineacetate monotherapy", 69thAnnual American Epilepsy Society Meeting, Dec. 4-8, 2015, Philadelphia, PA, USA, Article 1.182, 1 page.
McMurray et al., "Eslicarbazepine acetate as add-on treatment to antiepileptic monotherapy in patients with partial-onset seizures who previously did not respond to carbamazepine: Real-world evidence from the EPOS study", 69th AES Annual Meeting, Dec. 4-8, 2015, Philadelphia, Pennsylvania, USA, 1 page.
Karlsson et al., "Real-world data on eslicarbazepine acetate as add-on treatment to antiepileptic monotherapy in elderly patients (>60 years) with partial-onset seizures", 69th AES Annual Meeting, Dec. 4-8 2015, Philadelphia, Pennsylvania, USA, 1 page.
Bond et al.,"A comparison of instruments to measure depressive symptoms among patients with refractory partial-onset seizures", 67th American Academy of Neurology Annual Meeting, Apr. 18-25, 2015, Washington, DC, USA, Article P3.192, 1 page.
Bond et al., "Baseline depressive symptoms as predictive of seizure frequency reduction among epilepsy patients with partial-onset seizures: a pooled analysis of phase III clinical trials of adjunctive treatment with eslicarbazepine acetate", 57th American Academy of Neurology Annual Meeting, Apr. 18-25, 2015, Washington, DC, USA, Article P3.193, 1 page.
Cheng et al., "Efficacy of eslicarbazepine acetate as adjunctive treatment: sensitivity analyses of the impact of early termination", 69th Annual American Epilepsy Society Meeting, Dec. 4-8, 2015, Philadelphia, PA, USA, Article P1.185, 1 page.
Constantino et al., "Markers of bone turnover and lipid metabolism during eslicarbazepine acetate monotherapy, in patients taking or not taking enzyme-inducing antiepileptic drugs at baseline", 69th Annual American Epilepsy Society Meeting, Dec. 4-8, 2015, Philadelphia, PA, USA, Article P3.254, 1 page.
Gidal et al., "Abuse potential of antiepileptic drugs: a review using the VigiBaseTM pharmacovigilance database", 67th American Academy of Neurology Annual Meeting, Apr. 18-25, 2015, Washington, DC, USA, Article P1.233, 1 page.
McNulty et al., "Relationship between serum sodium level and treatment-emergent adverse events in patients taking eslicarbazepine acetate monotherapy: pooled analysis of two Phase III studies", 69th Annual American Epilepsy Society Meeting, Dec. 4-8, 2015, Philadelphia, PA, USA, Article P1.183, 1 page.

(56) References Cited

OTHER PUBLICATIONS

Pazdera et al., "Efficacy and safety of eslicarbazepine acetate monotherapy in patients converting from carbamazepine", 69th Annual American Epilepsy Society Meeting, Dec. 4-8, 2015, Philadelphia, PA, USA, Article P2.254, 1 page.
Moreira et al., "Status of a double-blind, randomized, active-controlled study to investigate the efficacy and safety of aslicarbazepine acetate as monotherapy in patients with newly diagnosed partial-onset seizures", 69th Annual American Epilepsy Society Meeting, Dec. 4-8, 2015, Philadelphia, PA, USA, 1 page.
Rosenfeld et al., "Tolerability of adjunctive eslicarbazepine acetate in elderly patients with epilepsy: an exploratory post-hoc analysis of three Phase III studies", 69th Annual American Epilepsy Society Meeting, Dec. 4-8, 2015, Philadelphia, PA, USA, Article P2.252, 1 page.
Trinka et al., "Mortality in Phase III studies of adjunctive and monotherapy eslicarbazepine acetate in patients with partial-onset seizures", 69th Annual American Epilepsy Society Meeting, Dec. 4-8, 2015, Philadelphia, PA, USA, Article P2.243, 1 page.
Velez et al., "Progression to adjunctive therapy among commercially-insured patients with partial-onse epilepsy", 67th American Academy of Neurology Annual Meeting, Apr. 18-25, 2015, Washington, DC, USA, Article P1.243, 1 page.
Velez et al., "A cost-comparison model to estimate the potential healthcare cost-impact of increased sodium channel blocker use among adjunctively-treated patients with partial-onset seizures", 67th American Academy of Neurology Annual Meeting, Apr. 18-25, 2015, Washington, DC, USA, Article P4.275, 1 page.
Velez et al., "Reasons for treatment discontinuation and switch in patients with epilepsy: a retrospective observational study in a US population", 67th American Academy of Neurology Annual Meeting, Apr. 18-25, 2015, Washington, DC, USA, Article P7.010, 1 page.
Wechsler et al., "Safety and tolerability of eslicarbazepine acetate monotherapy in patients converting from oxcarbazepine", 69th Annual American Epilepsy Society Meeting, Dec. 4-8, 2015, Philadelphia, PA, USA, Article 2.246, 1 page.
Villanueva et al., "Long-term safety and efficacy of eslicarbazepine acetate in patients with focal seizures: Results of the 1-year ESLIBASE retrospective study", Epilepsy Research, 2014, http://dx.doi.org/10.1016/j.eplepsyres.2014.04.014, 10 pages.
Chaves et al., "Efficacy of eslicarbazepine acetate as adjunctive therapy in adults with partial-onset seizures—ESLADOBA Study", Sinapse, 2015, vol. 15, No. 2, p. 94, with English translation (1 page).
Communication from European Patent Office enclosing a Third Party Observation for European Application No. 12762413.8 dated Jun. 20, 2016, 69 pages.
"Treatment", Modern Medical Encyclopedia, Saint Petersburg, Noriprint, 2004, pp. 1 and 280-284, with English translation (5 pages).
"Absence", Encyclopedic Medical Dictionary, Moscow, Medicina, 2001, pp. 1 and 6, with English translation (1 page).
Belousova et al, "Differential diagnosis", Childhood absence epilepesy, Letshashchy vrach, 2004, N1, pp. 1-5, with English translation (6 pages).
Bermejo et al., "Experience with eslicarbazepine in patients with hyponatraemia secondary to carbamazepine and oxcarbazepine", Rev Neural, 2015, vol. 61, pp. 47-48 with English translation (6 pages).
Sperling et al., "Conversion to Monotherapy with Eslicarbazepine Acetate in Adults with Partial-Onset Seizures—Results of a North-American Study", American Academy of Neurology 2014 Annual Meeting, Apr. 26-May 3, 2014, Philadelphia, PA, 2 pages.
Anastassopoulos et al., "Impact of Seizure Frequency Reduction on Health-Related Quality of Life Among Clinical Trial Subjects with Refractory Partial-Onset Seizures: A Pooled Analysis of Phase III Clinical Trials of Eslicarbazepine Acetate", American Academy of Neurology 2014 Annual Meeting, Apr. 26-May 3, 2014, Philadelphia, PA, 3 pages.

Vaisleib et al., "Effects of Eslicarbazepine Acetate on Cardiac Function in Patients with Refractory Partial-Onset Seizures: A Pooled Analysis of Three Phase III Controlled Studies", American Academy of Neurology 2014 Annual Meeting, Apr. 26-May 3, 2014, Philadelphia, PA, 2 pages.
Rogin et al., "Incidence of Allergic Reaction Adverse Events during Adjunctive Treatment with Eslicarbazepine Acetate in Patients with Refractory Partial-Onset Seizures: A Pooled Analysis of Three Phase III Placebo-Controlled Studies", American Academy of Neurology 2014 Annual Meeting, Apr. 26-May 3, 2014, Philadelphia, PA, 2 pages.
Benbadis et al., "Safety of Eslicarbazepine Acetate in Patients with Refractory Partial-Onset Seizures Treated With or Without Concomitant Carbamazepine: A Pooled Analysis of Three Phase III Controlled Studies", American Academy of Neurology 2014 Annual Meeting, Apr. 26-May 3, 2014, Philadelphia, PA, 2 pages.
Vazquez et al., "Co-administration of Carbamazepine with Eslicarbazepine Acetate Decreases Eslicarbazepine Exposure: A Population Pharmacokinetic Analysis", American Academy of Neurology 2014 Annual Meeting, Apr. 26-May 3, 2014, Philadelphia, PA, 2 pages.
Chung et al., "Efficacy of Eslicarbazepine Acetate in Patients with Refractory Partial-Onset Seizures Treated With or Without Concomitant Carbamazepine: A Pooled Analysis of Three Phase III Controlled Studies", American Academy of Neurology 2014 Annual Meeting, Apr. 26-May 3, 2014, Philadelphia, PA, 2 pages.
Gama et al., "Safety of eslicarbazepine acetate after 4 years of post-marketing in Europe", Sinapse, vol. 14, No. 1, 2014, p. 163, including English translation (1 page).
Costa et al., "Safety and efficacy of eslicarbazepine acetate after in elderly patients", Sinapse, vol. 14, No. 1, 2014, p. 163, including English translation (1 page).
Velez et al., "Association between depressive symptoms and seizure response among subjects with refractory partial-onset seizures in clinical trials of eslicarbazepine acetate", Epilepsy Currents, Jan./Feb. 2015, vol. 15, No. s1, p. 127.
Cramer et al., "Seizure severity among subjects with refractory partial-onset seizures: Analysis of the seizure severity questionnaire in a phase III trial of eslicarbazepine acetate", Epilepsy Currents, Jan./Feb. 2015, vol. 15, No. 31, p. 134.
Fakhoury et al., "Relationship between eslicarbazepine exposure and safety endoints for eslicarbazepine acetate monotherapy", Epilepsy Currents, Jan./Feb. 2015, vol. 15, No. s1, pp. 144-145.
Rogin et al., "Relationship between exposure and efficacy of eslicarbazepine acetate monotherapy", Epilepsy Currents, Jan./Feb. 2015, vol. 15, No. s1, pp. 145-146.
Rosenfeld et al., "Incidence of falls, fractures, and injuries with adjunctive eslicarbazepine acetate in patients with refractory partial-onset seizures: A pooled analysis of three placebo-controlled trials", Epilepsy Currents, Jan./Feb. 2015, vol. 15, No. s1, pp. 146-147.
Blum et al., "Hepatic safety of eslicarbazepine acetate: Summary of five phase II and three phase III adjunctive trials", Epilepsy Currents, Jan./Feb. 2015, vol. 15, No. s1, p. 147.
Andermann et al., "Eslicarbazepine acetate as adjunctive therapy for refractory partial-onset seizures: Analysis of cognitive adverse events", Epilepsy Currents, Jan./Feb. 2015, vol. 15, No. s1, p. 148.
Pazdera et al., "Eslicarbazepine acetate monotherapy in adults with partial-onset seizures: A pooled analysis of two randomized double-blind studies with use of a historical control", Epilepsy Currents, Jan./Feb. 2015, vol. 15, No. s1, pp. 148-149.
Harvey et al., "Relationship between eslicarbazepine exposure and efficacy of eslicarbazepine acetate adjunctive therapy", Epilepsy Currents, Jan./Feb. 2015, vol. 15, No. s1, p. 149.
Penovich et al., "Relationship between eslicarbazepine exposure and safety endpoints for eslicarbazepine acetate adjunctive therapy", Epilepsy Currents, Jan./Feb. 2015, vol. 15, No. s1, p. 150.
Abou-Khalil et al., "Eslicarbazepine acetate monotherapy: A population pharmacokinetic analysis", Epilepsy Currents, Jan./Feb. 2015, vol. 15, No. s1, pp. 150-151.
Benbadis et al., "Lack of Exacerbation of partial-onset seizures during adjunctive treatment with eslicarbazepine acetate: A pooled analysis of three phase III controlled trials", Epilepsy Currents, Jan./Feb. 2015, vol. 15, No. s1, p. 151.

(56) References Cited

OTHER PUBLICATIONS

Schoedel et al., "Evaluation of physical dependence potential following abrupt discontinuation of adjunctive eslicarbazepine acetate: A pooled analysis of adverse events from ten studies", Epilepsy Currents, Jan./Feb. 2015, vol. 15, No. s1, pp. 151-152.
Betts et al., "A systematic review and network meta-analysis of eslicarbazepine acetate and other recently-approved anti-epileptic drugs for adjunctive treatement of partial-onset seizures in adults", Epilepsy Currents, Jan./Feb. 2015, vol. 15, No. s1, p. 161.
O'Day et al., "Cost-effectiveness of eslicarbazepine acetate in refractory partial-onset epilepsy", Epilepsy Currents, Jan./Feb. 2015, vol. 15, No. s1, p. 162.
Biton et al., "Analysis of psychiatric adverse events in three phase III controlled trials of eslicarbazepine acetate as adjunctive therapy for refractory partial-onset seizures", Epilepsy Currents, Jan./Feb. 2015, vol. 15, No. s1, pp. 316-317.
Svendsen et al., "High retention rate in patients with refractory epilepsy treated with eslicarbazepine acetate", Epilepsy Currents, Jan./Feb. 2015, vol. 15, No. s1, pp. 318-319.
Sperling et al., "Long-term safety and efficacy of eslicarbazepine acetate monotherapy in adults with refractory partial-onset seizures: A one-year open-label extension study", Epilepsy Currents, Jan./Feb. 2015, vol. 15, No. s1, p. 323.
Krauss et al., "Improvement in seizure control during conversion to eslicarbazepine acetate monotherapy: A pooled analysis of two trials in adults with refractory partial-onset seizures", Epilepsy Currents, Jan./Feb. 2015, vol. 15, No. s1, pp. 324-325.
Abou-Khalil et al., "Incidence of treatment emergent adverse events in three phase III studies of adjunctive aslicarbazepine acetate, in patients taking or not taking lamotrigine at baseline", AES 2015 Annual Meeting Abstract Database. AESnet.org. https://www.aesnet.org/annual_meeting/abstracts/copyright, Abstract 1.186, 2015, 5 pages.
Anatassopoulos et al., "Predictors of 50% seizure frequency reduction among epilepsy patients with partial-onset seizures: Analysis of phase III trials of adjunctive treatment with eslicarbazepine acetate", AES 2015 Annual Meeting Abstract Database. AESnet.org. https://www.aesnetorg/annual_meeting/abstracts/copyright, Abstract 1.202, 2015, 3 pages.
Becser et al., "Clinical experience with eslicarbazepine acetate in adults focuing on elderly", AES 2015 Annual Meeting Abstract Database. AESnet.org. https://www.aesnet.org/annual_meeting/abstracts/copyright, Abstract 2.281, 2015, 3 pages.
Bond et al., "Change in depressive symptoms among patients with refractory partial-onset seizures treated with eslicarbazepine actetate monotherapy: A pooled analysis of clinical trials", AES 2015 Annual Meeting Abstract Database. AESnet.org. https://www.aesnet.org/annual_meeting/abstracts/copyright, Abstract 2.249, 2015, 3 pages.
Cheng et al., "Efficacy of eslicarbazepine acetate (ESL) as adjunctive treatment: Sensitivity analyses of the impact of early termination (ET)", AES 2015 Annual Meeting Abstract Database. AESnet.org. https://www.aesnet.org/annual_meeting/abstracts/copyright, Abstract 1.185, 2015, 3 pages.
Cid et al., "Health related quality of life and tolerability in patients under add-on treatment with eslicarbazepine", AES 2015 Annual Meeting Abstract Database. AESnet.org. https://www.aesnet.org/annual_meeting/abstracts/copyright, Abstract 3.273, 2015, 2 pages.
Constantino et al., "Markers of bone turnover and lipid metabolism during eslicarbazepine acetate (ESL) monotherapy, in patients taking or not taking enzyme-inducing antiepileptic drugs (EIAEDS) at baseline (BL)", AES 2015 Annual Meeting Abstract Database. AESnet.org. https://www.aesnet.org/annual_meeting/abstracts/copyright, Abstract 3.254, 2015, 5 pages.
Cramer et al., "Quality of life improvement among patients with refractory partial-onset seizures: A clinical trial analysis of patients who responded to eslicarbazepine acetate monotherapy", AES 2015 Annual Meeting Abstract Database. AESnet.org. https://www.aesnetorg/annual_meeting/abstracts/copyright, Abstract 1.182, 2015, 3 pages.

Gomez-Ibanez et al., "Safety and efficacy of eslicarbazepine acetate in elderly patients with focal epilepsy in real-life practice", AES 2015 Annual Meeting Abstract Database. AESnet.org. https://www.aesnet.org/annual_meeting/abstracts/copyright, Abstract 1.233, 2015, 1 page.
Gonzalez et al., "ESLI-Atlantico: Experience with eslicarbazepine acetate in focal epilepsies in Galicia, Spain", AES 2015 Annual Meeting Abstract Database. AESnet.org. https://www.aesnetorg/annual_meeting/abstracts/ copyright, Abstract 2.275, 2015, 2 pages.
Karlsson et al., "Real-world data on eslicarbazepine acetate as add-on treatment to antiepileptic monotherapy in elderly patients (>60 years) with partial-onset seizures", AES 2015 Annual Meeting Abstract Database. AESnet.org. https://www.aesnet.org/annual_meeting/abstracts/copyright, Abstract 2.261, 2015, 4 pages.
McNulty et al., "Relationship between serum sodium level ([NA+1]) and treatment-emergent adverse events (TEAES) in patients taking eslicarbazepine acetate (ESL) monotherapy: Pooled analysis of two phase III studies", AES 2015 Annual Meeting Abstract Database. AESnet.org. https://www.aesnet.org/annual_meeting/abstracts/copyright, Abstract 1.183, 2015, 4 pages.
Moreira et al., "Status of a double-blind, randomized, active-controlled study to investigate the efficacy and safety of eslicarbazepine acetate as monotherapy in patients with newly diagnosed partial-onset seizures", AES 2015 Annual Meeting Abstract Database. AESnet.org. https://www.aesnet.org/annual_meeting/abstracts/copyright, Abstract 3.264, 2015, 3 pages.
Pazdera et al., "Efficacy and safety of eslicarbazepine acetate (ESL) monotherapy in patients previously taking carbamazepine (CBZ)", AES 2015 Annual Meeting Abstract Database. AESnet.org. https://www.aesnet.org/annual_meeting/abstracts/copyright, Abstract 2.254, 2015, 3 pages.
Rosenfeld et al., "Tolerability of adjunctive eslicarbazepine acetate in elderly patients with epilepsy: An exploratory post-hoc analysis of three phase III studies", AES 2015 Annual Meeting Abstract Database. AESnet.org. https://www.aesnet.org/annual_meeting/abstracts/copyright, Abstract 2.252, 2015, 4 pages.
Tom et al., "Efficacy and tolerability of eslicarbazepine: Post marketing analysis", AES 2015 Annual Meeting Abstract Database. AESnet.org. https://www.aesnet.org/annual_meeting/abstracts/copyright, Abstract 2.248, 2015, 2 pages.
Trinka et al., "Mortality in phase III studies of adjunctive and monotherapy eslicarbazepine acetate in patients with partial-onset seizures", AES 2015 Annual Meeting Abstract Database. AESnet.org. https://www.aesnet.org/annual_meeting/abstracts/copyright, Abstract 2.243, 2015, 3 pages.
Wechsler et al., "Safety and tolerability of eslicarbazepine acetate (ESL) monotherapy in patients previously taking oxcarbazepine (OXC)", AES 2015 Annual Meeting Abstract Database. AESnet.org. https://www.aesnet.org/annual_meeting/abstracts/copyright, Abstract 2.246, 2015, 3 pages.
McMurray et al., "Eslicarbazepine acetate as add-on treatment to antiepileptic monotherapy in patients with partial-onset seizures who previously did not respond to carbamazepine: Real-world evidence from the EPOS study", AES 2015 Annual Meeting Abstract Database. AESnet.org. https://www.aesnet.org/annual_meeting/abstracts/copyright, Abstract 2.246, 2015, 4 pages.
Juan Jose Poza-Aldea, "A proposal for a model to replace carbamazepine or oxcarbazepine by eslicarbazepine acetate in clinical practice", Rev Neural., 2016, vol. 63, No. 5, pp. 219-223 with English abstract.
Brigo et al., "A common reference-based indirect comparison meta-analysis of eslicarbazepine versus lacosamide as add on treatments for focal epilepsy", Epilepsy Research, 2016, vol. 127, pp. 12-18.
Schmid et al., "Overnight switching from oxcarbazepine to eslicarbazepine acetate: an observational study", Acta Neurologica Scandinavica, 2016, pp. 1-5.
Holtkamp et al., "Real-world data on eslicarbazepine acetate as add-on to antiepileptic monotherapy", Acta Neurologica Scandinavica, 2016, vol. 134, No. 1, pp. 76-82.

(56) References Cited

OTHER PUBLICATIONS

Villanueva et al., "EPICON consensus: recommendations for proper management of switching to eslicarbazepine acetate in epilepsy", Neurologia, 2016, pp. 1-11, with English abstact.
Sperling et al., "Conversion to eslicarbazepine acetate monotherapy: A pooled analysis of 2 phase III studies", American Academy of Neurology, 2016, vol. 85, Vo. 12, pp. 1095-1102.
Tambucci et al., "Update on the role of eslicarbazepine acetate in the treatment of partial-onset epilepsy", Neuropsychiatric Disease and Treatment, 2016, vol. 12, pp. 1251-1260.
Servais et al., "Liquid chromatography separation of the chiral prodrug eslicarbazepine acetate and its main metabolites in polar organic mode. Application to their analysis after in vitro metabolism", Journal of Chromatography A, 2016, vol. 1467, pp. 306-311.
Losch et al., "Anticonvulsant add on therapy with Eslicarbazepine acetate: Results of the EPOS-study in adults in Germany", 2016, vol. 87, No. 10, pp. 1094-1099 with English Abstract.
Brigo et al., "Efficacy and tolerability of brivaracetam compared to lacosamide, eslicarbazepine acetate, and perampanel as adjunctive treatments in uncontrolled focal epilepsy: Results of an indirect comparison meta-analysis of RCTs", Seizure, 2016, vol. 42, pp. 29-37.
Marco Mula, "Third generation antiepileptic drug monotherapies in adults with epilepsy", Expert Review of Neurotherapeutics, 2016, vol. 16, No. 9, pp. 1087-1092.
Johannessen Landmark et al., "The Impact of Pharmacokinetic Interactions With Eslicarbazepine Acetate Versus Dxcarbazepine and Carbamazepine in Clinical Practice", The Drug Monit, Aug. 2016, vol. 38, No. 4, pp. 499-505.
Zelano et al., "Eslicarbazepine acetate for the treatment of partial epilepsy", Expert Opinion on Pharmacotherapy, 2016, vol. 17, No. 8, pp. 1165-1169.
Gierbolini et al., "Carbamazepine-related antiepileptic drugs for the treatment of epilepsy—a comparative review", Expert Opinion on Pharmacotherapy, 2016, vol. 17, No. 7, pp. 885-888.
Beck et al., "Linking Basic Science and Clinical Evidence in the Development of Eslicarbazepine Acetate", May 14-17, 2014, Documents presented at the Bial-Eisai satellite symposium at the 52nd Jahrestagung der Deutschen Gesellschaft fur Epileptologie e. V. (DGfE), www.epileptologie-bonn.de, English translation, 49 pages.
Shirley et al., "Eslicarbazepine Acetate Monotherapy: A Review in Partial-Onset Seizures", Drugs, 2016, vol. 76, No. 6, pp. 707-717.
Gilliam et al., "Changes in Quality of Life (QoL) and Depressive Symptoms in a Long-term Open-label Extension (OLE) of Eslicarbazepine Acetate (ESL) Monotherapy Studies in Adults with Refractory Partial-onset Seizures (POS) (P1.234)", American Academy Neurology 2015 Annual Meeting (Apr. 18-25, 2015), Neurology, Apr. 6, 2015, vol. 84, No. 14, Supplement P1.234, 2 pages.
Pazdera et al., "Eslicarbazepine Acetate (ESL) Monotherapy in Adults with Partial-Onset Seizures (POS): an Analysis of Pooled Data from Two Phase III Studies, with Use of a Historical Control (P1.250)", American Academy Neurology 2015 Annual Meeting(Apr. 18-25, 2015), Neurology, Apr. 6, 2015, vol. 84, No. 14, Supplement P1.250, 2 pages.
Sunkaraneni et al., "Population Pharmacokinetic (PK) Evaluation and Missed Dose Simulations for Eslicarbazepine.Acetate (ESL) Monotherapy (P4.258)", American Academy Neurology 2015 Annual Meeting (Apr. 18-25, 2015), Neurology, Apr. 6, 2015, vol. 84, No. 14, Supplement P4.258, 2 pages.
Rosenfeld et al., "Incidence of Falls, Fractures, and Injuries with Adjunctive Eslicarbazepine Acetate (ESL) in Patients with Refractory Partial-Onset Seizures (POS): a Pooled Analysis of Three Placebo-Controlled Trials (P4.277)", American Academy Neurology 2015 Annual Meeting (Apr. 18-25, 2015), Neurology, Apr. 6, 2015, vol. 84, No. 14, Supplement P4.277, 2 pages.
Bond et al., "Baseline Depressive Symptoms as Predictive of Seizure Frequency Reduction among Epilepsy Patients with Partial-Onset Seizures: A Pooled Analysis of Phase Iii Clinical Trials of Adjunctive Treatment with Eslicarbazepine Acetate (P3.193)", American Academy Neurology 2015 Annual Meeting (Apr. 18-25, 2015), Neurology, Apr. 6, 2015, vol. 84, No. 14, Supplement P3.193, 2 pages.
Bond et al., "A Comparison of Instruments to Measure Depressive Symptoms among Patients with Refractory Partial-Onset Seizures (P3.192)", American Academy Neurology 2015 Annual Meeting (Apr. 18-25, 2015), Neurology, Apr. 6, 2015, vol. 84, No. 14, Supplement P3.192, 2 pages.

* cited by examiner

TREATMENTS INVOLVING ESLICARBAZEPINE ACETATE OR ESLICARBAZEPINE

FIELD OF THE INVENTION

The invention relates to new therapeutic techniques involving eslicarbazepine acetate or eslicarbazepine.

BACKGROUND OF THE INVENTION

An epileptic seizure is defined as a clinical event associated with a transient, hypersynchronous neuronal discharge. The seizure represents only the symptom of a potential underlying brain pathology and not the actual disease. Epilepsy, in contradistinction to seizures, is a chronic disorder characterised by recurrent seizures. Epilepsy affects approximately 1% of the population.

Partial-onset seizures are a variety of epileptic seizure which affect only a part of the brain at onset. The seizure often remains localized, but may spread more widely throughout the brain. Partial seizures are generally divided into simple partial seizures, complex partial seizures and partial seizures secondarily generalised.

In contrast, absence seizures, also known as petit mal seizures, are a form of generalized seizure, which affects the whole of the brain, producing abnormal electrical activity throughout both hemispheres and, typically, loss of consciousness. Absence seizures are brief, generalized epileptic seizures with two characteristic features: (1) impairment of consciousness (absence) and (2) particular spike-and-slow wave discharges as measured by electroencephalography (EEG). The clinical manifestations of absence seizure may vary significantly among patients, and their etiology is not well defined or understood. Absence seizures generally occur more frequently in children than adults. Other varieties of generalized seizures include tonic-clonic seizures (grand mal), e.g. primary generalized tonic clonic seizures, myoclonic seizures, atonic seizures, clonic seizures and tonic seizures.

Eslicarbazepine acetate ((S)-10-acetoxy-10,11-dihydro-5H-dibenz[b,f]azepine-5-carboxamide) is a potent voltage-gated sodium channel blocker described, e.g., in WO-A-97/02250, WO-A-2006/121363, WO-A-2007/094694, WO-A-2008/088233, WO-A-2009/054743, WO-A-2011/014084, and WO-A-2011/031176, the contents of which applications are incorporated herein by reference. Eslicarbazepine acetate has been approved by the European Medicines Agency (EMA) for adjunctive therapy for partial-onset seizures, with or without secondary generalization, in adults with epilepsy.

Eslicarbazepine acetate is one of several drugs in the carboxamide dibenzazepine family. Other drugs in this family include oxcarbazepine (10,11-dihydro-10-oxo-5H-dibenz[b,f]azepine-5-carboxamide, OXC) and carbamazepine (5H-dibenz[b,f]azepine-5-carboxamide, CBZ).

Drugs in the carboxamide dibenzazepine family are used to treat partial-onset seizures. However, drugs in this class are known to aggravate general seizures, specifically absence seizures. Such aggravation of absence seizures is mediated via enhanced activity at the gamma amino butyric acid ($GABA_A$) receptor. Thus, Liu et al (J Pharmacol Exp Ther 319:790-798) explains that the activity of carbamazepine in aggravating absence seizures arises from the activity of the drug in enhancing activity at the $GABA_A$ receptor. Similarly, oxcarbazepine has also been linked with enhanced activity at the $GABA_A$ receptor and aggravation of absence seizures (Zheng T et al, Epilepsia, 50(1): 83-87, 2009).

Given that oxcarbazepine and carbamazepine aggravate absence seizures, it was therefore expected that other members of the carboxamide dibenzazepine family, such as eslicarbazepine acetate should not be used to treat patients who suffer from absence seizures. This is explained, for example, in the standard clinicians' reference book "The Treatment of Epilepsy", $3^{rd}$ edition, eds. Shorvon, Perucca & Engel, Chapter 38 (Almeida, L et al) (2009), which explains on page 497 that, based on the fact that eslicarbazepine acetate is structurally related to oxcarbazepine and carbamazepine, eslicarbazepine acetate may be expected to be potentially aggravating on some primary seizure types, particularly myoclonic and absence seizures.

Shorvon et al also explain at page 485 that the efficacy spectrum of eslicarbazepine acetate is restricted to partial epilepsies. Thus, there is no expectation in the art that eslicarbazepine acetate would have any effect in treating primary generalized seizures, such as absence seizures and primary generalized tonic clonic seizures. Many of the animal models which have historically been used to test antiepileptogenic properties of compounds are unable to distinguish between efficacy against primary generalized seizures and secondary generalized seizures. Further, many of the animal models may give results which are not directly applicable to the treatment of primary generalized seizures in human patients.

Primary generalized tonic clonic seizures in particular are not well understood, and their mechanism differs from that of secondary generalized tonic clonic seizures. Thus, whilst off label use of drugs licensed exclusively for treating partial seizures has been reported in some secondary generalized seizures, such use has not been reported in primary generalized seizures.

SUMMARY OF THE INVENTION

Eslicarbazepine acetate is metabolized in vivo in humans to the active metabolite, eslicarbazepine ((S)-10-hydroxy-10,11-dihydro-5H-dibenz[b,f]azepine-5-carboxamide), with R-licarbazepine and OXC as minor metabolites. Details can be found in "The Treatment of Epilepsy", $3^{rd}$ edition, eds. Shorvon, Perucca & Engel, Chapter 38 (Almeida, L et al) (2009), the contents of which are incorporated herein by reference.

Oxcarbazepine is also known to be metabolized in vivo in humans to eslicarbazepine and R-licarbazepine in a ratio of approximately 4:1.

It has now surprisingly been found that, contrary to the general understanding in the art, eslicarbazepine acetate and eslicarbazepine do not in fact aggravate absence seizures. Rather, they have antiepileptogenic activity in preventing or reducing the incidence of absence seizures.

Thus, it is a finding of the present invention that unlike oxcarbazepine and carbamazepine, eslicarbazepine is essentially devoid of effects upon $GABA_A$ receptor currents. It is another finding of the present invention that eslicarbazepine, in contrast to R-licarbazepine, oxcarbazepine and carbamazepine, effectively inhibits high and low affinity inward currents in T-type calcium channels. Transcriptional induction of T-type calcium channels is a critical step in epileptogenesis and neuronal vulnerability, so this finding demonstrates that eslicarbazepine and eslicarbazepine acetate will have antiepileptogenic effects and will be effective in preventing or reducing the incidence of absence seizures.

Advantageously, therefore, the findings of the present invention allow treatment of epilepsy, affective disorders, schizoaffective disorders, bipolar disorders, neuropathic pain and neuropathic pain related disorders, attention disorders, anxiety disorders, sensorimotor disorders, vestibular disorders, and fibromyalgia with eslicarbazepine or eslicarbazepine acetate in patients susceptible to absence seizures.

The epilepsy is typically partial onset seizures.

In a first embodiment, the present invention therefore provides a drug selected from eslicarbazepine acetate and eslicarbazepine, for use in treating or preventing a disorder selected from epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia, in a patient suffering from or susceptible to absence seizures.

In a second embodiment, the present invention provides a pharmaceutical composition for use in treating or preventing a disorder as defined herein, in a patient as defined herein, which pharmaceutical composition comprises a pharmaceutically acceptable carrier and, as active principle, a drug as defined herein.

In a third embodiment, the present invention provides use of a drug as defined herein, or a pharmaceutical composition as defined herein, in the manufacture of a medicament for use in treating or preventing a disorder as defined herein, in a patient as defined herein.

In a fourth embodiment, the present invention provides a method of treating or preventing a disorder as defined herein, in a patient as defined herein, which method comprises administering to said patient a safe and effective amount of a drug as defined herein, or a pharmaceutical composition as defined herein.

In a fifth embodiment, the present invention provides a method of treating or preventing a disorder as defined herein, which method comprises (a) selecting a patient as defined herein, and (b) administering to said patient a safe and effective amount of a drug as defined herein, or a pharmaceutical composition as defined herein.

In a sixth embodiment, the present invention provides a drug selected from eslicarbazepine acetate and eslicarbazepine, for use in treating or preventing, such as delaying the onset or reducing the incidence, severity or duration of absence seizures.

In a seventh embodiment, the present invention provides a pharmaceutical composition for use in preventing or reducing the incidence of absence seizures, which pharmaceutical composition comprises a pharmaceutically acceptable carrier and, as active principle, a drug as defined herein.

In an eighth embodiment, the present invention provides use of a drug as defined herein, or a pharmaceutical composition as defined herein, in the manufacture of a medicament for use in preventing or reducing the incidence of absence seizures.

In a ninth embodiment, the present invention provides a method of preventing or reducing the incidence of absence seizures in a patient, which method comprises administering to said patient a safe and effective amount of a drug as defined herein, or a pharmaceutical composition as defined herein.

DETAILED DESCRIPTION OF THE INVENTION

Figure 1:
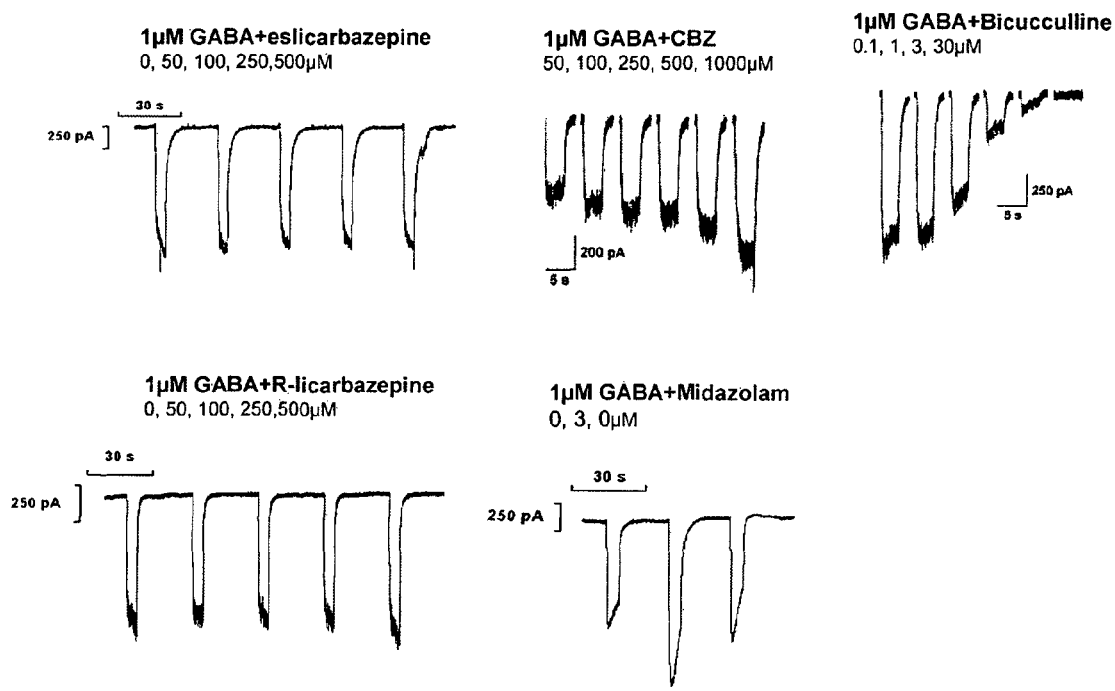
FIG. 1 shows representative current traces at $\alpha1\beta2\gamma2$ GABA receptors for eslicarbazepine, R-licarbazepine, carbamazepine (CBZ), bicucculine and midazolam in Ltk cells using a whole-cell patch-clamp technique.

As used herein, the words "treatment" and "treating" are to be understood as embracing treatment and/or amelioration and/or prevention of or reduction in aggravation/worsening of symptoms of a disease or condition as well as treatment of the cause of the disease or condition, and may include reversing, reducing, or arresting the symptoms, clinical signs, and underlying pathology of a condition in manner to improve or stabilise a subject's condition.

Reference to "prevention" and "preventing" a disease embraces prophylaxis and/or inhibition of the disease. The term "preventing" is art-recognized, and when used in relation to a condition, such as a local recurrence (e.g., pain), a disease such as cancer, a syndrome complex such as epilepsy or pain or any other medical condition, is well understood in the art, and includes administration of a composition which reduces the frequency of, or delays the onset of, symptoms of a medical condition in a subject relative to a subject which does not receive the composition. Thus, prevention of epilepsy includes, for example, delaying the onset or reducing the number (incidence), frequency, severity or duration of seizures, such as absence or partial onset seizures, in a population of patients receiving a prophylactic treatment relative to a control population untreated with eslicarbazepine or eslicarbazepine acetate, e.g., by a statistically and/or clinically significant amount. Prevention of pain, such as fibromyalgia, neuropathic pain or neuropathic pain related disorders includes, for example, reducing the magnitude of, or alternatively delaying, pain sensations experienced by subjects in a treated population versus a control population untreated with eslicarbazepine or eslicarbazepine acetate. Prevention of bipolar disorders includes, for example, reducing the number of manic, hypomanic, cyclothymic, psychotic or depressive episodes in a treated population versus a control population untreated with eslicarbazepine or eslicarbazepine acetate.

Typically, the patient is a human patient.

Affective disorders include depression, pre-menstrual dysphoric disorder, post-partum depression, post-menopausal depression, anorexia nervosa, bulimia nervosa, and neurodegeneration-related depressive symptoms.

Schizoaffective disorders include schizodepressive syndromes, schizophrenia, extreme psychotic states, schizomanic syndromes, dysphoric and aggressive behavior, episodic dyscontrol or intermittent explosive disorder, and borderline personality disorder.

Bipolar disorders include bipolar disorder and unstable bipolar disorder with rapid fluctuations (rapid cyclers), manic-depressive disorders, acute mania, mood episodes, and manic and hypomanic episodes.

Attention disorders include attention deficit hyperactivity disorders (attention deficit disorders) and other attention disorders such as autism.

Anxiety disorders include conditions social anxiety disorders, post-traumatic stress disorder, panic, obsessive-compulsive disorder, alcoholism, drug withdrawal syndromes, and cravings.

Neuropathic pain and neuropathic pain-related disorders are described in. WO-A-2007094694 and include neuropathic pain and associated hyperalgesia, including trigeminal, herpetic, post-herpetic and tabetic neuralgia, diabetic neuropathic pain, migraines, tension-type headaches, causalgia, and deafferentation syndromes such as brachial plexus avulsion.

Sensorimotor disorders include restless legs syndrome, spasticity, hemifacial spasm, nocturnal paroxysmal dystonia, brain ischemia associated motor and sensitive deficits, Parkinson's disease and parkinsonian disorders, antipsychotic-induced motor deficits, tardive dyskinesia, episodic nocturnal wandering, and myotonia.

Vestibular disorders include tinnitus or other inner ear/cochlear excitability related diseases, such as neuronal loss, hearing loss, sudden deafness, vertigo, and Meniere's disease.

Fibromyalgia is a well-known disorder, and is described in, for example, WO-A-2011/014084.

Typically, the disorder is epilepsy, particularly partial-onset seizures. Partial-onset seizures are a well-known disorder typically associated with epilepsy. Partial seizures may also be referred to as focal or localized seizures. Partial seizures include simple partial seizures and complex partial seizures. Partial-onset seizures may present with or without secondary generalization.

Typically, the disorder is partial onset seizure, neuropathic pain, a neuropathic pain-related disorder or fibromyalgia.

Typically, the drug is eslicarbazepine acetate.

Preferably, the drug is eslicarbazepine acetate, and the disorder is partial-onset seizures.

Absence seizures are a well-known type of seizure, more commonly occurring in females. Typically, therefore, the patient is female. Absence seizures are generally divided into typical and atypical absence seizures.

Typical absence seizures usually occur in patients having idiopathic generalised epilepsies and an EEG of patients having typical absence seizures shows fast >2.5 Hz generalised spike-wave discharges, for example greater than about 3 Hz. Cognitive impairment is not often seen with typical absence seizures.

Atypical absence seizures typically occur only in children suffering from severe symptomatic or cryptogenic epilepsies, who usually also present with learning difficulties. Such patients typically also suffer from frequent seizures of other types such as atonic, tonic and myoclonic. Onset and termination of an atypical absence seizure is not so abrupt as in typical absence seizures, and changes in tone are more pronounced. EEG of patients having atypical absence seizures usually shows slow <2.5 Hz spike and slow wave patterns, for example from about 1 to about 2 Hz. The discharge experienced in an atypical seizure is heterogeneous, often asymmetrical and may include irregular spike and slow wave complexes, fast and other paroxysmal activity. Background interictal EEG is usually abnormal.

Children and adolescents are more susceptible to absence seizures than adults. Many children who suffer from absence seizures grow out of them as they get older. Typically, therefore, the patient susceptible to absence seizures is a child or adolescent. Typically, the patient is under about 20 years old, preferably under about 18 years old, more preferably under about 17 years old, even more preferably under about 16 years old, even more preferably under about 15 years old, even more preferably under about 14 years old, for example, from about 2 to about 13 years old, from about 9 to about 13 years old, from about 10 to about 15 years old, from about 4 to about 8 years old, or from about 5 to about 7 years old. Thus, typically, the patient has not yet reached puberty.

Patients susceptible to absence seizures will typically have been diagnosed as suffering from absence seizures. Patients susceptible to absence seizure will more typically have previously suffered from at least one seizure such as an absence seizure, myclonic seizure or tonic-clonic seizure, preferably an absence seizure.

Patients susceptible to absence seizures may have a family history of epilepsy and/or may already have experienced other seizures types prior to experiencing absence seizures, for example generalized tonic-clonic seizures (which may often be experienced on awakening) or myoclonic seizures. Thus, typically, the patient has a family history of epilepsy. Therefore patients susceptible to absence seizures, and in particular atypical absence seizures, may show interictal abnormalities on electro-encephalogram (EEG), and may have previously experienced multiple types of seizure, and may show cognitive abnormalities or mental retardation.

Particular genetic abnormalities may be present in patients susceptible to absence seizures, for example, the γ-aminobutyric acid $(GABA)_A$ receptor γ-2 subunit mutation R43Q. Thus, typically, the patient has the R43Q mutation in the γ-aminobutyric acid $(GABA)_A$ receptor γ-2 subunit. Patients susceptible to absence seizures may or may not be photosensitive.

Idiopathic generalized epilepsies which present with absence seizures include childhood (or infantile) absence epilepsy, juvenile absence epilepsy, myoclonic absence epilepsy, juvenile myoclonic epilepsy and Lennox-Gastaut syndrome. Other proposed generalized epilepsies associated with absence seizures include perioral myoclonus with absences, Jeavons syndrome (eyelid myoclonus with absences) and idiopathic generalised epilepsy with phantom absences. Thus, typically, the patient is suffering from or susceptible to childhood absence epilepsy, juvenile absence epilepsy, myoclonic absence epilepsy, juvenile myoclonic epilepsy, Lennox-Gastaut syndrome, perioral myoclonus with absences, Jeavons syndrome or idiopathic generalised epilepsy with phantom absences. Preferably, the patient is suffering from or susceptible to childhood absence epilepsy, juvenile absence epilepsy, myoclonic absence epilepsy, juvenile myoclonic epilepsy or Lennox-Gastaut syndrome.

Primary generalized tonic clonic seizures are a well-known type of seizure, which like absence seizures affect the whole brain. Primary generalized tonic clonic seizures involve two phases, the tonic phase and the clonic phase. In the tonic phase, patients typically display a rigid contracture of muscles, including respiratory muscles. The tonic phase is usually brief. In the clonic phase, patients typically display rhythmic shaking. The clonic phase is usually longer than the tonic phase. Together, a generalized tonic clonic seizure is also called a grand mat seizure.

Primary generalized tonic clonic seizures are idiopathic, i.e. they occur without any apparent cause and are typically not preceded by a partial seizure. Primary generalized tonic clonic seizures may present on awakening.

The drugs for use in the present invention may be administered as monotherapy treatment for the indication or with other drug(s) as adjunct therapy for the indication, as described in more detail below. In the case of adjunct therapy, the drugs for use in the present invention may be administered simultaneously or sequentially with the other drug(s), for example in fixed dose combination or in separate doses.

The drugs for use in the present invention may be administered by any suitable route to provide a therapeutic effect against partial-onset seizures, neuropathic pain or fibromyalgia. Thus, they can be administered orally, for example as tablets, capsules, caplets, troches, lozenges, aqueous or oily suspensions, dispersible powders or granules. The drugs may also be administered parenterally, whether subcutaneously, intravenously, intramuscularly, intrasternally, transdermally or by infusion techniques. The drugs may also be administered as suppositories.

Typically, the drugs are for oral administration.

In one embodiment, the drugs are administered as a tablet.

In another embodiment, the drugs are administered as a suspension. This embodiment is explained further in WO-A-2011/031176, the content of which is incorporated herein by reference.

In a further embodiment, the drugs are administered as a granule or sprinkle formulation. This embodiment is explained further in WO-A-2012/091593, the content of which is incorporated herein by reference.

The drugs for use in the present invention may be administered once a day, or more than once a day, for example two, three or four times a day. Typically, the drugs are for once daily administration. This is explained further in WO-A-2006/121363, the content of which is incorporated herein by reference.

Dosages will vary depending on, e.g., the individual, the mode and frequency of administration, and the nature and severity of the condition to be treated. A clinician having ordinary skill in the art can readily determine and prescribe the effective amount required.

Typical doses for a patient will range from 1 mg per kilogram to 50 mg per kilogram of body weight per day, preferably 5 mg per kilogram to 45 mg per kilogram of body weight per day, more preferably 10 mg per kilogram to 40 mg per kilogram of body weight per day, even more preferably 5, 10, 15, 20, 25 or 30 mg per kilogram of body weight per day. A typical daily oral dose of the drugs is from 100 mg to 1.200 mg per day, preferably from 200 mg to 800 mg per day, more preferably from 400 to 600 mg per day. EMA approved dosages of eslicarbazepine acetate for adjunctive therapy for partial-onset seizures, with or without secondary generalisation, in adults with epilepsy are 400 mg, 800 mg, or 1200 mg daily.

Eslicarbazepine acetate and eslicarbazepine are particularly effective adjuncts for use with other drugs. The findings of the present invention mean that eslicarbazepine acetate and eslicarbazepine are particularly advantageous for use in treating or preventing a disorder selected from epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia in a patient susceptible to absence seizures who is being treated with a drug which may cause or aggravate their absence seizures. Thus, for example, in the case of epilepsy (such as partial onset seizure), a patient may be receiving a second antiepileptic drug which may cause or aggravate absence seizures, for example carbamazepine, oxcarbazepine, vigabatrin, tiagabine, phenytoin, phenobarbital, gabapentin, or pregabalin. By substituting eslicarbazepine acetate and eslicarbazepine for part of one of these drugs, an antiepileptic effect may still be achieved without aggravating absence seizures.

Eslicarbazepine acetate and eslicarbazepine may also be used in combination with another drug (adjunct therapy) which is effective against epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia. Such drugs will be well known to the skilled person. In the case of epilepsy (such as partial onset seizure), clorazepate, clonazepam, ethosuximide, felbamate, fosphenytoin, lacosamide, lamotrigine, levetiracetam, primidone, topiramate, valproate semisodium, valproic acid, and zonisamide are all approved by the FDA, for treating epilepsy, but are not counterindicated against absence seizures. However, eslicarbazepine acetate and eslicarbazepine may also be administered as monotherapy for the indication.

In a second embodiment, the present invention provides a pharmaceutical composition for use in treating or preventing a disorder as defined herein, in a patient as defined herein, which pharmaceutical composition comprises a pharmaceutically acceptable carrier and as active principle, a drug as defined herein.

Said pharmaceutical composition typically contains at least 50 wt % of a drug as defined herein. More typically, it contains at least 80 wt % of a drug as defined herein. Preferred pharmaceutical compositions are sterile and pyrogen free.

Eslicarbazepine acetate and eslicarbazepine are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, povidone, carboxymethylcellulose or polyvinyl pyrrolidone; disaggregating agents, e.g. starch, alginic acid, alginates, croscarmellose soldium or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in any known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, xanthan gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, a wetting agent, for example polyoxyethylene stearate, an antimicrobial agent, such as methylparaben or propylparaben, and if desired, a suitable amount of lidocaine hydrochloride.

Solutions for injection or infusion may contain as a carrier, for example, sterile water or preferably they may be in the form of sterile, aqueous, isotonic saline solutions.

Typically, the pharmaceutical composition is in the form of a tablet, granule (sprinkle) formulation (i.e. for sprinkling on food) or suspension. Suitable suspensions are described in WO-A-2011031176.

In a third embodiment, the present invention provides use of a drug as defined herein, or a pharmaceutical composition as defined herein, in the manufacture of a medicament for use in treating or preventing a disorder as defined herein, in a patient as defined herein.

Typically, in this embodiment, the medicament is for coadministration with a second drug which may cause or aggravate absence seizures, for example carbamazepine, oxcarbazepine, vigabatrin, tiagabine, phenytoin, phenobarbital, gabapentin, or pregabalin.

Typically, in this embodiment, the medicament is for coadministration with one or more additional medications (adjunct therapy) for treatment of epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia. In the case of epilepsy (such as partial onset seizure), the additional medicament is typically chosen from clorazepate, clonazepam, ethosuximide, felbamate, fosphenytoin, lacosamide, lamotrigine, levetiracetam, primidone, topiramate, valproate semisodium, valproic acid, and zonisamide. However, the medicament may also be administered as monotherapy for the indication.

In a fourth embodiment, the present invention provides a method of treating or preventing a disorder as defined herein, in a patient as defined herein, which method comprises administering to said patient a safe and effective amount of a drug as defined herein, or a pharmaceutical composition as defined herein.

Typically, in this embodiment, the drug is coadministered with a second drug which may cause or aggravate absence seizures, for example carbamazepine, oxcarbazepine, vigabatrin, tiagabine, phenytoin, phenobarbital, gabapentin, or pregabalin.

Typically, in this embodiment, the drug is coadministered with one or more additional medications (adjunct therapy) for treatment of epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia. In the case of epilepsy (such as partial onset seizure), the additional medicament is typically chosen from clorazepate, clonazepam, ethosuximide, felbamate, fosphenytoin, lacosamide, lamotrigine, levetiracetam, primidone, topiramate, valproate semisodium, valproic acid, and zonisamide. However, the drug may also be administered as monotherapy for the indication.

In a fifth embodiment, the present invention provides a method of treating or preventing a disorder as defined herein, which method comprises (a) selecting a patient as defined herein, and (b) administering to said patient a safe and effective amount of a drug as defined herein, or a pharmaceutical composition as defined herein.

Typically, in this embodiment, the drug is coadministered with a second drug which may cause or aggravate absence seizures, for example carbamazepine, oxcarbazepine, vigabatrin, tiagabine, phenytoin, phenobarbital, gabapentin, or pregabalin.

Typically, in this embodiment, the drug is coadministered with one or more additional medications (adjunct therapy) for treatment of epilepsy such as partial-onset seizures, affective disorders, schizoaffective disorders, bipolar disorders, neuropathic pain and neuropathic pain related disorders, attention disorders, anxiety disorders, sensorimotor disorders, vestibular disorders, and fibromyalgia. In the case of epilepsy, the additional medicament is typically chosen from clorazepate, clonazepam, ethosuximide, felbamate, fosphenytoin, lacosamide, lamotrigine, levetiracetam, primidone, topiramate, valproate semisodium, valproic acid, and zonisamide. However, the drug may also be administered as monotherapy for the indication.

As discussed above, eslicarbazepine acetate and eslicarbazepine have advantageous antiepileptogenic properties which make them effective in preventing or reducing the incidence of absence seizures.

In a sixth embodiment, therefore, the present invention provides a drug selected from eslicarbazepine acetate and eslicarbazepine, for use in preventing or reducing the incidence of absence seizures. Typically the drug provides control of absence seizures, even when complicated by other seizure types, for example by reducing the frequency and/or severity of absence seizures.

Typically, the drug is eslicarbazepine acetate.

Typically, the drug is for use in treating a patient who is suffering from or susceptible to absence seizures, as defined herein.

Typical dosages of the drug are as defined above.

Typically, in this embodiment, the drug is for coadministration with one or more additional medications (adjunct therapy) for treatment of absence seizures. Such medications are well-known to the skilled person, and include sodium valproate, valproic acid, ethosuximide and lamotrigine. However, the drug may also be administered as monotherapy for the indication.

In a seventh embodiment, the present invention provides a pharmaceutical composition for use in preventing or reducing the incidence of absence seizures, which pharmaceutical composition comprises a pharmaceutically acceptable carrier and, as active principle, a drug as defined herein.

Typical pharmaceutical compositions and pharmaceutically acceptable carriers are as defined herein.

In an eighth embodiment, the present invention provides use of a drug as defined herein, or a pharmaceutical composition as defined herein, in the manufacture of a medicament for use in preventing or reducing the incidence of absence seizures.

Typically, the medicament is for use in preventing or reducing the incidence of absence seizures in a patient who is suffering from or susceptible to absence seizures, as defined herein.

Typically in this embodiment, the medicament is for coadministration with one or more additional medications (adjunct therapy) for treatment of absence seizures, as defined herein. However, the medicament may also be administered as monotherapy for the indication.

In a ninth embodiment, the present invention provides a method of preventing or reducing the incidence of absence seizures in a patient, which method comprises administering to said patient a safe and effective amount of a drug as defined herein, or a pharmaceutical composition as defined herein.

Typically, the patient is a patient suffering from or susceptible to absence seizures, as defined herein.

Typically in this embodiment, the drug is coadministered with one or more additional medications (adjunct therapy) for treatment of absence seizures, as defined herein. However, the drug may also be administered as monotherapy for the indication.

The antiepileptogenic properties of eslicarbazepine acetate and eslicarbazepine also make them effective in preventing or reducing the incidence of primary generalized tonic clonic seizures.

In a tenth embodiment the present invention provides a drug selected from eslicarbazepine acetate and eslicarbazepine, for use in preventing or reducing the incidence of primary generalized tonic clonic seizures.

Typically the drug provides control of primary generalized tonic clonic seizures, even when complicated by other seizure types, for example by reducing the frequency and/or severity of primary generalized tonic clonic seizures.

Typically, the drug is eslicarbazepine acetate.

Typically, the drug is for use in treating a patient who is suffering from or susceptible to primary generalized tonic clonic seizures, as defined herein.

Typical dosages of the drug are as defined above.

Typically, in this embodiment, the drug is for coadministration with one or more additional medications (adjunct therapy) for treatment of primary generalized tonic clonic seizures. Such medications are well-known to the skilled person, and include sodium valproate, valproic acid, ethosuximide, lamotrigine, topiramate, zonisamide, levetiracetam and rufinamide. Preferably agents for coadministration are sodium valproate, valproic acid, ethosuximide and lamotrigine. However, the drug may also be administered as monotherapy for the indication.

In an eleventh embodiment, the present invention provides a pharmaceutical composition for use in preventing or reducing the incidence of primary generalized tonic clonic seizures, which pharmaceutical composition comprises a pharmaceutically acceptable carrier and, as active principle, a drug as defined herein.

Typical pharmaceutical compositions and pharmaceutically acceptable carriers are as defined herein.

In a twelfth embodiment, the present invention provides use of a drug as defined herein, or a pharmaceutical composition as defined herein, in the manufacture of a medicament for use in preventing or reducing the incidence of primary generalized tonic clonic seizures.

Typically, the medicament is for use in preventing or reducing the incidence of primary generalized tonic clonic seizures in a patient who is suffering from or susceptible to primary generalized tonic clonic seizures, as defined herein.

Typically in this embodiment, the medicament is for coadministration with one or more additional medications (adjunct therapy) for treatment of primary generalized tonic clonic seizures, as defined herein. However, the medicament may also be administered as monotherapy for the indication.

In a thirteenth embodiment, the present invention provides a method of preventing or reducing the incidence of primary generalized tonic clonic seizures, in a patient, which method comprises administering to said patient a safe and effective amount of a drug as defined herein, or a pharmaceutical composition as defined herein.

Typically, the patient is a patient suffering from or susceptible to primary generalized tonic clonic seizures, as defined herein.

Typically in this embodiment, the drug is coadministered with one or more additional medications (adjunct therapy) for treatment of primary generalized tonic clonic seizures, as defined herein. However, the drug may also be administered as monotherapy for the indication.

The treatments described herein are also effective in treating patients who are suffering from both absence seizures and primary generalized tonic clonic seizures.

In a fourteenth embodiment the present invention provides a drug selected from eslicarbazepine acetate and eslicarbazepine, for use in preventing or reducing the incidence of both absence seizures and primary generalized tonic clonic seizures.

Typically the drug provides control of both absence seizures and primary generalized tonic clonic seizures, even when complicated by other seizure types, for example by reducing the frequency and/or severity of absence seizures and/or primary generalized tonic clonic seizures.

Typically, the drug is eslicarbazepine acetate.

Typically, the drug is for use in treating a patient who is suffering from or susceptible to absence seizures and/or primary generalized tonic clonic seizures, as defined herein.

Typical dosages of the drug are as defined above.

Typically, in this embodiment, the drug is for coadministration with one or more additional medications (adjunct therapy) for treatment of absence seizures and/or primary generalized tonic clonic seizures. Such medications are well-known to the skilled person, and include sodium valproate, valproic acid, ethosuximide, lamotrigine, topiramate, zonisamide, levetiracetam and rufinamide. Preferably agents for coadministration are sodium valproate, valproic acid, ethosuximide and lamotrigine. However, the drug may also be administered as monotherapy for the indication.

In a fifteenth embodiment, the present invention provides a pharmaceutical composition for use in preventing or reducing the incidence of both absence seizures and primary generalized tonic clonic seizures, which pharmaceutical composition comprises a pharmaceutically acceptable carrier and, as active principle, a drug as defined herein.

Typical pharmaceutical compositions and pharmaceutically acceptable carriers are as defined herein.

In a sixteenth embodiment, the present invention provides use of a drug as defined herein, or a pharmaceutical composition as defined herein, in the manufacture of a medicament for use in preventing or reducing the incidence of both absence seizures and primary generalized tonic clonic seizures.

Typically, the medicament is for use in preventing or reducing the incidence of absence seizures and/or primary generalized tonic clonic seizures in a patient who is suffering from or susceptible to absence seizures and/or primary generalized tonic clonic seizures, as defined herein.

Typically in this embodiment, the medicament is for coadministration with one or more additional medications (adjunct therapy) for treatment of absence seizures and/or primary generalized tonic clonic seizures, as defined herein. However, the medicament may also be administered as monotherapy for the indication.

In a seventeenth embodiment, the present invention provides a method of preventing or reducing the incidence of both absence seizures and primary generalized tonic clonic seizures, in a patient, which method comprises administering to said patient a safe and effective amount of a drug as defined herein, or a pharmaceutical composition as defined herein.

Typically, the patient is a patient suffering from or susceptible to absence seizures and/or primary generalized tonic clonic seizures, as defined herein.

Typically in this embodiment, the drug is coadministered with one or more additional medications (adjunct therapy) for treatment of absence seizures and/or primary generalized tonic clonic seizures, as defined herein. However, the drug may also be administered as monotherapy for the indication.

The following non-limiting Examples illustrate the invention.

EXAMPLES

Example 1

Carbamazepine (CBZ) aggravates absence seizures in 'generalized absence epilepsy rats from. Strasbourg'. One putative mechanism for the aggravation is through its reported potentiation of $GABA_A$ currents. A study was carried out to determine the effect of eslicarbazepine, R-licarbazepine and carbamazepine on sub-maximal GABA currents in Ltk cells stably expressing α1β2γ2, α2β2γ2, α3β2γ2 or α5β2γ2 GABA-receptors. The whole-cell patch-clamp technique was used to investigate the effects of the test compounds on GABAA receptors.

Used Ltk cells were stably transfected with recombinant $GABA_A$ cDNAs: α1β2γ2, α2β2γ2, α3β2γ2 or α5β2γ2 (B'SYS GmbH, Switzerland). Cells were maintained in a humidified atmosphere (95% relative humidity) with 5% $CO_2$ and were grown in D-MEM/F-12 (1×, liquid, with GlutaMax 1) supplemented with 9% foetal bovine serum and 0.9% Penicillin/Streptomycin solution (Gibco BRL). For the electrophysiological experiments cells were cultivated, at a density that enabled single cells to be measured, in medium without antibiotics or antimycotics. Cells were tested 24-48 hours following induction of transgene expression with dexamethasone.

Cells were continuously perfused with bath solution (NaCl 137 mM, KCl 4 mM, $CaCl_2$ 1.8 mM, $MgCl_2$ 1 mM, D-Glucose 10 mM HEPES 10 mM, pH 7.4). The whole-cell patch clamp recordings from transfected Ltk cells (voltage-clamped at a holding potential of −80 mV) were made using a EPC-7, HEKA Electronics amplifier. GABA inward-currents were measured upon application of 1 or 2 μM GABA to patch-clamped cells (at an EC5). Eslicarbazepine, R-licarbazepine, carbamazepine, midazolam (positive allosteric modulator of the $GABA_A$ receptor) or bicuculline (negative allosteric modulator of the $GABA_A$ receptor) were applied by perfusion with GABA.

SigmaPlot 8.02 was used to calculate the means±SEM of relative peak'current blockade for each test item. Analysis of Variance (ANOVA) with post test multisample comparison (Dunnett) was conducted with GraphPad Prism 4 Software.

The effect of eslicarbazepine and R-licarbazepine on GABA inward current stimulation measured on Ltk cells stably transfected with α1β2γ2, α2β2γ2, α3β2γ2 or α5β2γ2 GABA receptors is shown in the following table.

TABLE 1

| | | Current stimulation (%) | | | | | | | |
|---|---|---|---|---|---|---|---|---|---|
| | | α1β2γ2 | | α2β2γ2 | | α3β2γ2 | | α5β2γ2 | |
| Compound | (μM) | Mean ± SEM | n | Mean ± SEM | n | Mean ± SEM | n | Mean ± SEM | n |
| Vehicle | | 108.11 ± 3.40 | 3 | 96.95 ± 1.27 | 5 | 101.25 ± 1.92 | 5 | 95.40 ± 0.53 | 5 |
| Eslicarbazepine | 50 | 103.3 ± 1.96 | 3 | 91.58 ± 2.69 | 5 | 95.61 ± 4.75 | 5 | 95.18 ± 2.18 | 5 |
| | 100 | 95.92 ± 0.83 | 3 | 97.04 ± 2.65 | 5 | 97.93 ± 4.22 | 5 | 93.89 ± 0.60 | 5 |
| | 250 | 97.82 ± 1.13 | 3 | 88.56 ± 3.24** | 5 | 96.44 ± 2.16 | 5 | 93.52 ± 1.75 | 5 |
| | 500 | 99.39 ± 0.80 | 3 | 89.80 ± 4.01 | 5 | 91.63 ± 5.56 | 5 | 89.65 ± 3.44 | 5 |
| R-Licarbazepine | 50 | 99.85 ± 1.18 | 3 | 96.48 ± 2.11 | 5 | 99.53 ± 2.65 | 5 | 96.13 ± 0.57 | 5 |
| | 100 | 92.53 ± 4.53 | 3 | 97.03 ± 2.27 | 5 | 100.38 ± 1.56 | 5 | 94.09 ± 1.27 | 5 |
| | 250 | 91.73 ± 4.69 | 3 | 93.79 ± 3.09 | 5 | 102.94 ± 3.34 | 5 | 97.24 ± 1.58 | 5 |
| | 500 | 95.83 ± 6.63 | 3 | 87.75 ± 1.94* | 5 | 97.35 ± 2.91 | 5 | 92.25 ± 1.29 | 5 |
| Midazolam | 3 | 184.81 ± 32.93* | 3 | na | | na | | na | |
| Bicucculline | 1 | na | | 27.85 ± 3.21 | 5 | 34.16 ± 3.99 | 5 | 39.65 ± 4.34 | 5 |

Vehicle was 0.2% DMSO for α1β2γ2 and 0.4% for all the other GABA receptors.
*Significantly different from vehicle (P < 0.01).
**Significantly different from vehicle (P < 0.05)

The effect of carbamazepine and bicucculline on GABA inward current stimulation measured on Ltk cells stably transfected with α1β2γ2, α2β2γ2, α3β2γ2 or α5β2γ2 GABA receptors is shown in the following table.

TABLE 2

| | | Current stimulation (%) | | | | | | | |
|---|---|---|---|---|---|---|---|---|---|
| | | α1β2γ2 | | α2β2γ2 | | α3β2γ2 | | α5β2γ2 | |
| Compound | (μM) | Mean ± SEM | n | Mean ± SEM | n | Mean ± SEM | n | Mean ± SEM | n |
| Vehicle | | 96.19 ± 3.71 | 11 | 97.58 ± 3.59 | 10 | 100.29 ± 5.92 | 6 | 95.25 ± 4.61 | 6 |
| Carbamazepine | 50 | 104.30 ± 5.02 | 6 | 97.94 ± 3.34 | 5 | 93.32 ± 4.07 | 6 | 103.82 ± 1.50 | 6 |
| | 100 | 117.38 ± 4.94 | 6 | 111.36 ± 2.65 | 5 | 112.76 ± 5.40 | 6 | 103.83 ± 4.53 | 6 |
| | 250 | 115.68 ± 5.31 | 6 | 109.03 ± 7.61 | 5 | 131.06 ± 9.39 | 6 | 93.59 ± 4.30 | 6 |
| | 500 | 132.42 ± 5.31* | 6 | 103.60 ± 7.61 | 5 | 120.27 ± 11.81 | 6 | 80.65 ± 5.86 | 6 |
| | 1000 | 150.26 ± 15.48* | 6 | 104.18 ± 2.66 | 5 | 166.66 ± 21.00* | 6 | 63.01 ± 4.50* | 6 |
| Bicuccullin | 0.1 | 70.48 ± 3.19** | 5 | 62.71 ± 2.57* | 5 | 66.06 ± 3.05 | 5 | 60.16 ± 3.45* | 5 |
| | 1 | 24.28 ± 1.70* | 5 | 16.40 ± 2.24* | 5 | 25.82 ± 5.11* | 5 | 10.26 ± 1.77* | 5 |
| | 3 | 8.23 ± 1.01* | 5 | 2.15 ± 1.09* | 5 | 10.45 ± 1.39* | 5 | 5.87 ± 2.47* | 5 |
| | 30 | 0.35 ± 0.49* | 5 | 1.87 ± 1.40* | 5 | 3.07 ± 1.42* | 5 | 1.68 ± 0.73* | 5 |

Vehicle was 0.4% DMSO.
*Significantly different from vehicle (P < 0.01).
**Significantly different from vehicle (P < 0.05)

Representative current traces at α1β2γ2 GABA receptors for eslicarbazepine, R-licarbazepine, carbamazepine (CBZ), bicucculine and midazolam are shown as FIG. 1.

Eslicarbazepine and R-licarbazepine, in contrast to carbamazepine, can be seen to be devoid of effects upon sub-maximal GABA currents.

Example 2

T-type channels are critically important in controlling the excitability of the postsynaptic compartment of neurons, both in normal and epileptic neurons (Huguenard J R. (1996) Annu Rev Physiol 58, 329-348). Aberrant bursting is seen in CA1 hippocampal neurons from epileptic animals that is mediated by increased expression of T-type Ca2+ channels (Sanabria E R G, Su H, Yaari Y. (2001) J Physiol 532, 205-216). Transcriptional induction of T-type calcium channels ($Ca_v3.2$) is a critical step in epileptogenesis and neuronal vulnerability (Su H, Sochivko D, Becker A, Chen J, Jiang Y Yaari Y, Beck H. (2002) J Neurosci, 22, 3645-3655).

A study was carried out to determine the effect of eslicarbazepine. R-licarbazepine, oxcarbazepine (OXC) and carbamazepine (CBZ) on human T-type calcium channels $hCa_v3.2$ currents recorded from stably transfected HEK 293 cells. The whole-cell patch-clamp technique was used to investigate the effects of eslicarbazepine, R-licarbazepine, oxcarbazepine and carbamazepine on $hCa_v3.2$ calcium channels stably expressed in HEK cells.

HEK 293 obtained from European Collection of Animal Cell Culture Cells were maintained in a humidified atmosphere (95% relative humidity) with 5% $CO_2$ and were grown in D-MEMF-12 (1× liquid with GlutaMax I, Gibco BRL) supplemented with 9% foetal bovine serum (Gibco-BRL), 0.9% Penicillin/Streptomycin solution (Gibco BRL) and 100 μg/ml Geneticin. Cells were stably transfected with $hCa_v3.2$ cDNA.

Cells were continuously perfused with bath solution (NaCl 137 mM, KCl 4 mM, $CaCl_2$ 1.8 mM, $MgCl_2$ 10 mM, D-Glucose 10 mM HEPES 10 mM, pH 7.4). Calcium inward currents were measured upon depolarization of the cell membrane to −25 mV for 50 ms from a holding potential of −80 mV. This voltage protocol was run at intervals of 10 s until stabilization of evoked $hCa_v3.2$ currents. Once control recordings were accomplished, cells were perfused with bath solution containing eslicarbazepine, R-licarbazepine, oxcarbazepine or carbamazepine (0.3 to 1000 μM) or the reference compounds valproic acid (1 mM) or mibefradil (0.01-10 μM). Vehicle was either bath solution or 0.2% DMSO.

SigmaPlot 8.02 was used to calculate the means±SEM of relative peak current blockade for each compound. Analysis of variance (ANOVA) with post test multisample comparison (Dunnett) was conducted with GraphPad Prism 4 Software. $IC_{50}$ were calculated with the equation:

$$current_{peak, relative} = \left(y1 + \frac{(100-y1)}{1+10^{([LogIC50(1)-X] \cdot H1)}}\right) + \left(y2 + \frac{(y1-y2)}{1+10^{([LogIC50(2)-X] \cdot H2)}}\right) - y1$$

where 1 refers to the high affinity fit and 2 to the low affinity fit. X is the compound concentration, y1/y2 is the remaining peak current amplitude, IC50(1)/IC50(2) is the concentration of drug at half maximal inhibition and H1/H2 is the Hill coefficient for the fit.

The effect of eslicarbazepine, R-licarbazepine, carbamazepine (CBZ), oxcarbazepine (OXC) and mibefradil on calcium peak currents on HEK 293 cells expressing the $hCa_v3.2$ channels is shown in the following table.

TABLE 3

| Concentration (μM) | Relative current amplitude (%) | | | | | |
|---|---|---|---|---|---|---|
| | eslicarbazepine | | R-licarbazepine | CBZ | | |
| | Mean ± SEM | n | Mean ± SEM | Mean ± SEM | OXC | Mibefradil | n |
| 0.01 | | | | | | 84.72 ± 3.20 | 5 |
| 0.1 | | | | | | 57.32 ± 3.97* | 5 |
| 0.3 | 86.99 ± 1.56* | 5 | 98.42 ± 1.33 | 5 | | 99.10 ± 0.57 | 5 | |
| 1 | 81.61 ± 1.31* | 5 | 92.43 ± 1.41 | 5 | | 98.04 ± 0.63 | 5 | 19.11 ± 2.58* | 5 |
| 3 | 76.21 ± 1.61* | 9 | 88.21 ± 1.03* | 9 | | 94.82 ± 0.93 | 5 | |
| 10 | 71.22 ± 2.40* | 9 | 82.92 ± 1.29* | 9 | | 92.83 ± 2.76 | 5 | 9.13 ± 2.31* | 5 |
| 25 | | | | | 87.58 ± 2.94 | 5 | |
| 30 | 73.04 ± 1.64* | 5 | 78.21 ± 2.14* | 5 | | 90.14 ± 1.98 | 5 | |
| 50 | 61.44 ± 4.96* | 4 | 73.86 ± 3.78* | 4 | 76.53 ± 5.48 | 5 | |
| 100 | 54.68 ± 6.35* | 4 | 71.61 ± 1.68* | 4 | 69.98 ± 4.47 | 5 | |
| 250 | 46.92 ± 6.64* | 4 | 64.52 ± 3.05* | 4 | 59.47 ± 6.06* | 5 | |
| 500 | 51.83 ± 4.77* | 8 | 58.10 ± 2.74* | 7 | 45.66 ± 7.45* | 5 | |
| 1000 | 45.48 ± 4.94* | 4 | 39.37 ± 5.33* | 3 | | | |

Control values obtained with vehicle were 97.35 ± 1.28 (n = 8). Remaining current obtained with 10 mM valproic acid was 65.15 ± 2.05% (n = 8).
*Significantly different from control (P < 0.01).

Figure 2:
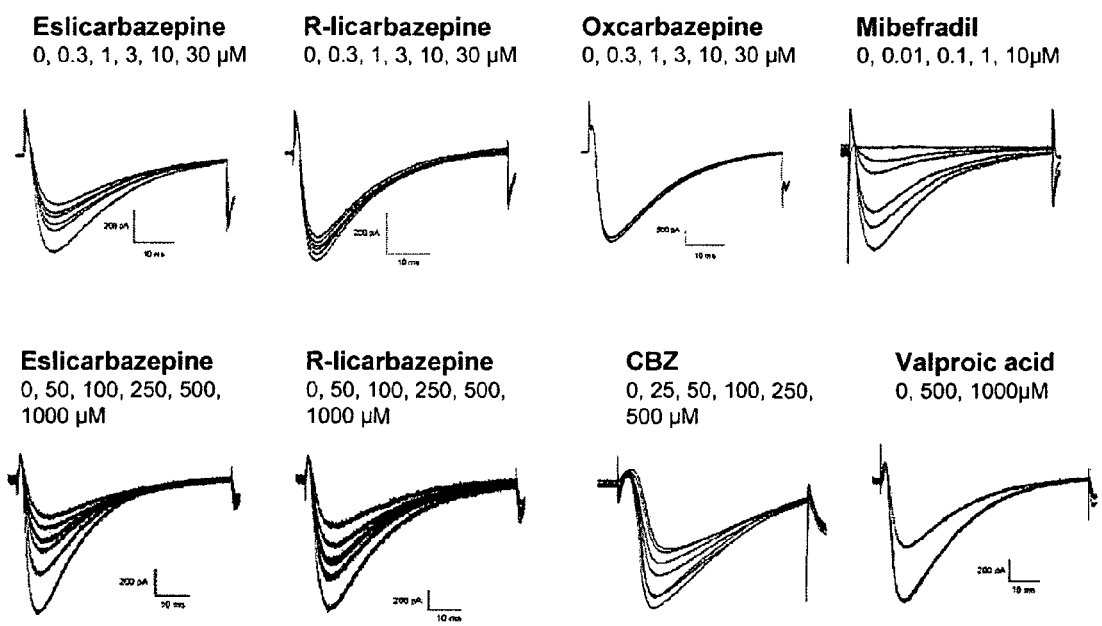
FIG. 2 shows representative current traces for eslicarbazepine, R-licarbazepine, oxcarbazepine (OXC) and carbamazepine (CBZ) and mibefradil at the high affinity (top) and low affinity (bottom) binding sites for $hCa_v3.2$ calcium channels stably expressed in HEK cells using a whole-cell patch-clamp technique.

Representative current traces for eslicarbazepine, R-licarbazepine, oxcarbazepine and carbamazepine and mibefradil at the high affinity (top) and low affinity (bottom) binding sites are shown as FIG. 2.

Figure 3:
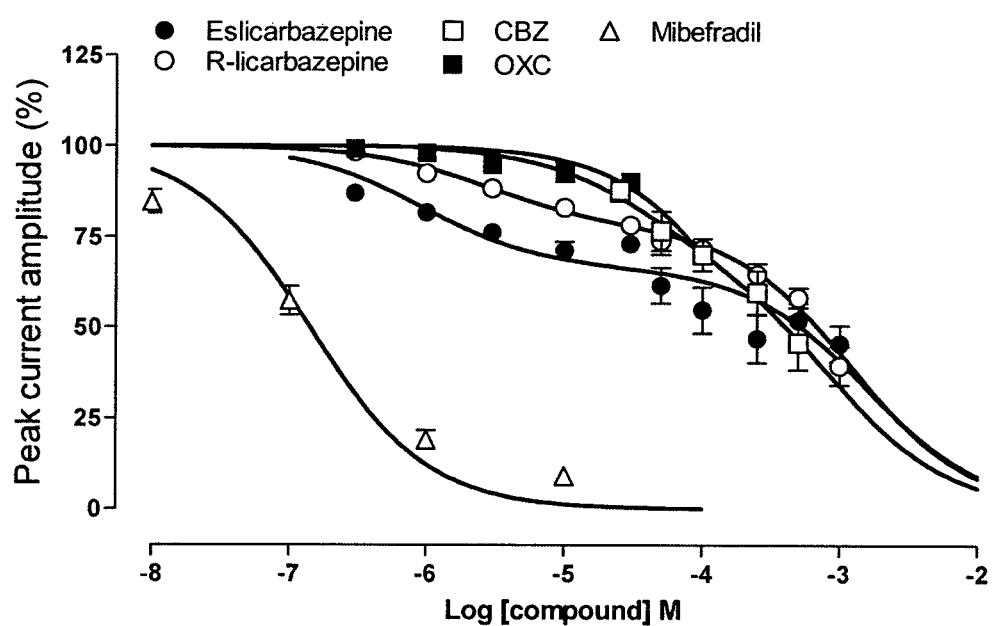
FIG. 3 shows Inhibition dose-response curves for the blockade of $hCa_v3.2$ currents by eslicarbazepine, R-licarbazepine, CBZ, OXC and mibefradil in HEK cells using a whole-cell patch-clamp technique.

Inhibition dose-response curves for the blockade of $hCa_v3.2$ currents by eslicarbazepine, R-licarbazepine, CBZ, OXC and mibefradil is shown as FIG. 3.

$IC_{50}$ values were determined as follows from inhibition curves for eslicarbazepine, R-licarbazepine, carbamazepine (CBZ), oxcarbazepine (OXC) and mibefradil.

TABLE 4

| | $hCa_v3.2$ $IC_{50}$ (μM) | |
|---|---|---|
| Compounds | High affinity | Low affinity |
| Eslicarbazepine | 0.43 | 62.61 |
| R-licarbazepine | 6.54 | 883.10 |
| CBZ | 27.10 | 711.20 |

TABLE 4-continued

| | hCa$_v$3.2 IC$_{50}$ (μM) | |
|---|---|---|
| Compounds | High affinity | Low affinity |
| OXC | nc | nc |
| Mibefradil | 0.14 | nc | nc—not calculated

It can be seen that eslicarbazepine, R-licarbazepine and carbamazepine dose dependently inhibited hCa$_v$3.2 calcium peak currents (Table 3 and FIG. 2). The inhibition curves were best fitted with a two site binding model and a constant remaining current amplitude. A block of high affinity occurs with an IC$_{50}$ of 0.43 μM, 6.54 or 27.10 μM for eslicarbazepine, R-licarbazepine and carbamazepine, respectively (table of IC$_{50}$ values above and FIG. 3). A further block occurs at higher concentrations of the test items, with an IC$_{50}$ of 62.61 μM for eslicarbazepine, 883.10 μM for R-licarbazepine and 711.20 μM for carbamazepine (table of IC$_{50}$ values above and FIG. 3). Oxcarbazepine, up to 30 μM, was devoid of effect on hCa$_v$3.2 currents.

(Regarding the reference compounds, 1 mM valproic acid blocked calcium peak currents by 66.15±2.05 (n=8 cells) and mibefradil dose dependently inhibited hCa$_v$3.2 calcium peak currents with an IC$_{50}$ of 143.7 nM.)

The obtained data demonstrates that eslicarbazepine, in contrast to R-licarbazepine, carbamazepine and oxcarbazepine, effectively inhibits high and low affinity hCa$_v$3.2 inward currents.

Example 3

Following oral administration of oxcarbazepine, eslicarbazepine acetate, eslicarbazepine and R-licarbazepine in rats, all compounds result in oxcarbazepine. Therefore to test the effects of oral administration of eslicarbazepine acetate, mice models are used.

Administration of eslicarbazepine and eslicarbazepine acetate in the following models is tested:
(a) Absence seizure induced by γ-butyrolactone
  Absence seizure arises from aberrant thalamocortical. Oscillatory burst firing of thalamocortical neurons induces spike and wave discharges (SWDs), and the generation of this firing results from Ca$^{2+}$ influx into the thalamocortical neurons via low-threshold calcium channels. γ-Hydroxybutyric acid (GHB) as well as various γ-aminobutyric acid GABA receptor agonists are reported to induce absence seizures. GHB has been proposed as a neurotransmitter/neuromodulator that acts via its own receptor. The systemic injection of GHB into mice elicits rhythmic 3 Hz SWD, the EEG hallmark of absence seizures, and represents a well established and widely used pharmacological model of this nonconvulsive epilepsy. Ryu et al (2007) Journal of Neurochemistry, 102:646-656
(b) Succinic semialdehyde dehydrogenase deficiency
  The succinic semialdehyde dehydrogenase (SSADH) null mouse represents a viable animal model for human SSADH deficiency and is characterised by markedly elevated levels of both GHB and GABA in brain, blood, and urine. GHB is known to induce absence-like seizures and absence seizures have been reported to occur in children with SSADH deficiency. Sequential electrocorticographic (ECoG) and prolonged video ECoG recordings from chronically implanted electrodes were performed on SSADH/, SSADH+/, and SSADH+/+ mice from postnatal day (P) 10 to (P) 21. Spontaneous, recurrent absence-like seizures appeared in the SSADH/ during the second week of life and evolved into generalized convulsive seizures late in the third week of life that were associated with an explosive onset of status epilepticus which was lethal. The seizures in SSADH null mice were consistent with typical absence seizures in rodent with 7 Hz spike-and-wave discharge (SWD) recorded from thalamocortical circuitry. Cortez et al (2004) Pharmacology, Biochemistry & Behaviour 79:547-553.
(c) Stargazer Mouse model.
  The stargazer (stg) mutant mouse harbors a transposon insertion in the second intron of the calcium channel γ2 subunit (cacng2) locus, disrupting transcription of the gene. The stg mouse has proved to be an exceptionally informative mutant, exhibiting several disorders including spontaneous absence seizure, cerebellar ataxia, and head tossing. Ryu et al (2008) Journal of Neurochemistry 104:1260-1270
(d) C3H/He mouse model
  The inbred mouse strain C3H/He exhibits spontaneous absence seizures characterized by spike and wave discharges (SWD) on the electroencephalogram concomitant with behavioural arrest. Tokuda et a (2009) Genes, Brain & Behaviour 8:283-289

Results show that eslicarbazepine acetate and eslicarbazepine are effective in controlling seizures in these models.

Example 4

Clinical trial study: A randomised double-blind, placebo controlled, trial assesses the efficacy and safety of adjunctive eslicarbazepine acetate in primary generalised tonic clonic seizure (PGTCS) in human patients in accordance with established methods.

Methods: Men and women are selected for trial according to standard inclusion criteria in the field including the following:
Subject is male or female and aged 6-65 years.
Subject has ≥3 PGTCS over the two months before screening and during the eight weeks Baseline Period with at least one seizure in each one month period. PGTCS must occur in the context of Idiopathic Generalized Epilepsy (IGE) and may be accompanied by other primary generalized seizures, provided these are also consistent with a diagnosis of IGE.
Subject is taking a stable regimen of one or two other Antiepileptic Drugs (AEDs) for at least two weeks prior to Visit 1 (start of the Baseline Period).
Subject has a clinical diagnosis of any type of idiopathic generalized epilepsy which has PGTCS (and which may be accompanied by other generalized seizure types), according to the International League Against Epilepsy (ILAE) Classification of Epileptic Seizures (1981) and the ILAE Classification of Epilepsies and Epileptic Syndromes (1989). Diagnosis should have been established by clinical history, electroencephalogram (EEG) and computed tomography/magnetic resonance imaging (CT/MRI) of the brain consistent with idiopathic generalized epilepsy. CT/MRI scan should have been performed within five years of the screening visit or, if not available from this period, should be performed in the Baseline Period.

EEG should have been performed within one year of the screening visit or, if not available from this period, should be performed in the Baseline Period.

Subject has a body weight ≥20 kg.

Patients may be excluded from trial in accordance with known exclusion criteria in the field.

Patients selected for trial are randomised to treatment sequences comprising eslicarbazepine acetate at effective dosage and placebo administered by conventional means.

Trial endpoints assessed clinical criteria are as follows:

time to withdrawal after randomisation;
time to first, second, or other seizure after randomisation (time to first seizure after randomisation allows determination of the proportion of patients at different time points who remain seizure free);
time to achieving remission (e.g. at six months, one year, or two years);
change in seizure severity;
change in seizure frequency;
percentage response to treatment (response defined as a 50% or greater reduction in seizure frequency);
change in seizure-free interval;
change in seizure duration;
change in seizure pattern;
change in functional capacity; and
patient-related quality of life.

CONCLUSION

Treatment with eslicarbazepine acetate in patients suffering from or susceptible to PGTCS leads to improved clinical effects indicating usefulness of eslicarbazepine acetate adjunct or monotherapy in treating PGTCS.

The invention claimed is:

1. A method of treating partial-onset seizures in a patient who is suffering from or susceptible to absence seizures, which method comprises:
administering to said patient a safe and effective amount of eslicarbazepine acetate.

2. The method according to claim 1, wherein the patient is female.

3. The method according to claim 1, wherein the patient is under sixteen years of age.

4. The method according to claim 1, wherein the patient has not reached puberty.

5. The method according to claim 1, wherein the patient has previously suffered from at least one seizure selected from the group consisting of absence seizure, myoclonic seizure and tonic-clonic seizure.

6. The method according to claim 1, wherein the patient has a family history of epilepsy.

7. The method according to claim 1, wherein the patient has the R43Q mutation in the γ-aminobutyric acid $(GABA)_A$ receptor γ-2 subunit.

8. The method according to claim 1, wherein the patient is suffering from or susceptible to at least one disease or syndrome selected from the group consisting of: childhood absence epilepsy, juvenile absence epilepsy, myoclonic absence epilepsy, juvenile myoclonic epilepsy, Lennox Gastaut syndrome, perioral myoclonus with absences, Jeavons syndrome and idiopathic generalized epilepsy with phantom absences.

9. The method according to claim 1, wherein the patient is receiving a second drug which may cause or aggravate absence seizures.

10. The method according to claim 9, wherein the second drug is selected from the group consisting of:
carbamazepine, oxcarbazepine, vigabatrin, tiagabine, phenytoin, phenobarbital, gabapentin, and pregabalin.

11. The method according to claim 1, wherein the eslicarbazepine acetate is administered orally.

12. The method according to claim 1, wherein the eslicarbazepine acetate is administered once daily.

13. The method according to claim 1, wherein the patient receives one or more additional medications for treatment of partial-onset seizures.

14. The method according to claim 13, wherein the additional medication is selected from the group consisting of:
clorazepate, clonazepam, ethosuximide, felbamate, fosphenytoin, lacosamide, lamotrigine, levetiracetam, primidone, topiramate, valproate semisodium, valproic acid, and zonisamide.

15. The method according to claim 1, wherein the eslicarbazepine acetate is administered to the patient as an adjunct therapy.

16. A method of treating partial-onset seizures in a patient who is suffering from or susceptible to absence seizures, which method comprises:
administering to said patient a safe and effective amount of a pharmaceutical composition, which comprises a pharmaceutically acceptable carrier and a safe and effective amount of eslicarbazepine acetate as an active ingredient.

17. The method according to claim 16, wherein the pharmaceutical composition is in the form of a tablet, a suspension or a sprinkle formulation.

18. A method of treating partial onset seizures, which method comprises:
(a) selecting a patient who is suffering from or susceptible to absence seizures; and
(b) administering to said patient a safe and effective amount of eslicarbazepine acetate, or a pharmaceutical composition, which comprises a pharmaceutically acceptable carrier and a safe and effective amount of eslicarbazepine acetate as an active ingredient.

19. A method of reducing the incidence of absence seizures in a patient, which method comprises administering to said patient a safe and effective amount of eslicarbazepine acetate, or a pharmaceutical composition, which comprises a pharmaceutically acceptable carrier and a safe and effective amount of eslicarbazepine acetate as an active ingredient.

* * * * *